(12) United States Patent
Guan

(10) Patent No.: US 7,169,594 B2
(45) Date of Patent: Jan. 30, 2007

(54) DIAGNOSIS AND TREATMENT OF DISEASES ARISING FROM DEFECTS IN THE TUBEROUS SCLEROSIS PATHWAY

(75) Inventor: Kun-Liang Guan, Ann Arbor, MI (US)

(73) Assignee: Regents of the University of Michigan

( * ) Notice: Subject to any disclaimer, the term of this patent is extended or adjusted under 35 U.S.C. 154(b) by 369 days.

(21) Appl. No.: 10/639,263

(22) Filed: Aug. 12, 2003

(65) Prior Publication Data

US 2004/0106637 A1    Jun. 3, 2004

Related U.S. Application Data

(60) Provisional application No. 60/402,718, filed on Aug. 12, 2002.

(51) Int. Cl.
*C12N 9/12* (2006.01)

(52) U.S. Cl. ..................................... 435/194

(58) Field of Classification Search ...................... None
See application file for complete search history.

(56) References Cited

U.S. PATENT DOCUMENTS

2004/0009968 A1    1/2004    Binch et al. ........... 514/207.05

FOREIGN PATENT DOCUMENTS

WO    WO 93/19752    10/1993

OTHER PUBLICATIONS

Tee et al., Proc. Natl. Acad. Sci. 99:13571-13576 (2002).
Onda et al., J. Clin.Invest. 104, 687-695 (1999).
Au et al., Am. J. Hum. Genet. 62, 286-294 (1998).
Kobayashi, T. et al., Proc. Natl Acad. Sci. USA 98, 8762-8767 (2001).
Gao and Pan, Genes Dev. 15, 1383-1392 (2001).
Ito et al., Cell 96, 529-539 (1999.
Potter et al., Cell 105, 357-368 (2001).
Tapon et al., Cell 105, 345-355 (2001).
Kozma et al., Bioessays 24, 65-71 (2002).
Stocker and Hafen, Curr. Opin. Genet. Dev. 10, 529-535 (2000).
Shioi, T. et al., EMBO J. 19, 2537-2548 (2000).
Shioi, T. et al., Mol. Cell. Biol. 22, 2799-2809 (2002).
Weinkove and Leevers, Curr. Opin. Genet. Dev. 10, 75-80 (2000).
DeChiara et al., Nature 345, 78-80 (1990).
Shima et al., EMBO J. 17, 6649-6659 (1998).
Neshat, et al., Proc. Natl Acad. Sci. USA 98, 10314-10319 (2001).
Schmelzle and Hall, Cell 103, 253-262 (2000).
Shah et al., Am. J. Physiol. Endocrinol. Metab.279, E715-E729 (2000).
Sonenberg, and Gingras, Curr. Opin. Cell Biol. 10, 268-275 (1998).
Podsypanina, et al., Proc. Natl Acad. Sci. USA 98, 10320-10325 (2001).
Aoki et al., Proc. Natl Acad. Sci. USA 98, 136-141 (2001).
Burgering et al., Nature 376 pg. 599-609 (1995).
Scott et al., Proc. Natl Acad. Sci. USA 95, 7772-7777 (1998).
Sekulic, A. et al. Cancer Res.60, 3504-3513 (2000).
Kwiatkowski et al. Hum. Mol. Genet. 11, 525-534.
Tuttle, et al. Nature Med. 7, 1133-1137 (2001).
Reynolds et al., J. Biol. Chem. 277, 17657-17662 (2002).
Nave et al., Biochem J. 344, 427-431 (1999).
Peterson et al., Proc. Natl Acad. Sci. USA 96, 4438-4442 (1999).
Brown et al., Nature 377:441-446 (1995).
Hara et al., J. Biol. Chem. 273:14484-94 (1998).
Goncharova et al., J. Biol Chem. 277:30958-30967 (2002).
Kenerson et al., Cancer Res. 62:5645-5650 (20002).
Browne and Proud, Eur. J. Biochem. 269:5360-5368 (2002).
Proud, Eur. J. Biochem. 269:5338-5349 (2002).
Hardie et al., Ann. Rev. Biochem. 67:821-855 (1998).
Corton et al., Eur. J. Biochem. 229:558-565 (1995).
Kimura et al., Genes Cells 8:65-79 (2003).
Krause et al., Eur. J. Biochem. 269:3751-3759 (2002).
Shioi et al., Circulation 107:1664-1670 (2003).
Potter and Xu, Curr. Opin. Genet. Dev. 11:279-286 (2001).
Dennis et al. Science 294, 1102-1105 (2001).
Weng et al., Mol. Cell. Biol. 15, 2333-2340 (1995).
Schalm et al., Curr. Biol. 12, 632-639 (2002).
Fingar et al., Genes Dev. 16:1472-1487 (2002).
Inoki et al., Nat. Cell Bio. 4:648-657 (2002).
Miloloza et al., J Neuropathol Exp. Neurol Feb. 2002 61(2):154-63.

*Primary Examiner*—Christopher R. Tate
*Assistant Examiner*—Amanda P. Wood
(74) *Attorney, Agent, or Firm*—Medlen & Carroll, LLP

(57) ABSTRACT

The present invention relates to compositions and methods for identifying abnormalities in TSC signaling pathways. In particular, the present invention relates to methods of diagnosing and treating disorders such as tuberous sclerosis, which are caused by mutations in the TSC genes. The present invention further relates to methods and compositions for treating cancers mediated by TSC signaling disorders.

10 Claims, 20 Drawing Sheets a b

DIAGNOSIS AND TREATMENT OF DISEASES ARISING FROM DEFECTS IN THE TUBEROUS SCLEROSIS PATHWAY

The present application claims priority to U.S. Provisional Application Ser. No. 60/402,718, filed Aug. 12, 2002, herein incorporated by reference.

This invention was made with government support under Grant No GM51586 awarded by the National Institutes of Health. The Government has certain rights in the invention.

FIELD OF THE INVENTION

The present invention relates to compositions and methods for identifying abnormalities in TSC signaling pathways. In particular, the present invention relates to methods of diagnosing and treating disorders such as tuberous sclerosis, which are caused by mutations in the TSC genes. The present invention further relates to methods and compositions for treating cancers mediated by TSC signaling disorders.

BACKGROUND

Tuberous Sclerosis (TSC) is a relatively common inheritable genetic disorder that occurs in approximately 1 in 6000 of the population and is characterized by the development of hamartomas in a variety of organs (Young & Povey, Mol. Med. Today 4, 313–319 (1998)). Common clinical symptoms include seizures, mental retardation, autism, kidney failure, facial angiofibromas and cardial Rhabdomyomas (Gomez, Ann. NY Acad. Sci. 615, 1–7 (1991)). In addition, many affected individuals have cyst-like areas within certain skeletal regions, particularly bones of the fingers and toes (phalanges). Characteristic skin lesions include sharply defined areas of decreased skin coloration (hypopigmentation) that may develop during infancy and relatively small reddish nodules that may appear on the cheeks and nose beginning at approximately age four. These reddish lesions eventually enlarge, blend together (coalesce), and develop a wart-like appearance (sebaceous adenomas). Additional skin lesions may also develop, including flat, "coffee-colored" areas of increased skin pigmentation (café-au-lait spots); benign, fibrous nodules (fibromas) arising around or beneath the nails; or rough, elevated, "knobby" lesions (shagreen patches) on the lower back.

TSC may be present at birth, but signs of the disorder can be subtle and full symptoms may take some time to develop. As a result, TSC is frequently unrecognized and misdiagnosed for years. In most cases the first clue to recognizing TSC is the presence of seizures or delayed development. In other cases, the first sign may be white patches on the skin (hypomelanotic macules).

Diagnosis of the disorder is based on a careful clinical exam in combination with computed tomography (CT) or magnetic resonance imaging (MRI) of the brain, which may show tubers in the brain, and an ultrasound of the heart, liver, and kidneys, which may show tumors in those organs. Diagnosis also involves a careful examination of the skin for the wide variety of skin features, the fingernails and toenails for ungual fibromas, the teeth and gums for dental pits and/or gum fibromas, and the eyes for dilated pupils. A Wood's lamp or ultraviolet light may be used to locate the hypomelantic macules, which are sometimes hard to see on infants and individuals with pale or fair skin.

In infants TSC may be suspected if the child has cardiac rhabdomyomas or seizures (infantile spasms) at birth. With a careful examination of the skin and brain, it may be possible to diagnose TSC in a very young infant. However, most children are not diagnosed until later in life when their seizures begin and other symptoms such as facial angiofibromas appear.

There is no specific treatment for tuberous sclerosis. Treatment is symptomatic and may include anticonvulsant therapy for seizures, dermabrasion and laser removal techniques for the skin manifestations, drug therapy for neurobehavioral problems, treatment of high blood pressure caused by the kidney problems, and surgery to remove growing tumors.

The prognosis for individuals with tuberous sclerosis varies depending on the severity of symptoms. There is no cure. Those individuals with mild symptoms generally do well and live long productive lives, while individuals with the more severe form may have serious disabilities. In rare cases, seizures, infections, or tumors in vital organs may cause complications in some organs such as the kidneys and brain that can lead to severe difficulties and even death.

Improved TSC early diagnostics are needed to allow for earlier treatment. Additional therapeutics are also needed. Preferred therapeutics are those that treat symptoms systemically.

SUMMARY OF THE INVENTION

The present invention relates to compositions and methods for identifying abnormalities in TSC signaling pathways. In particular, the present invention relates to methods of diagnosing and treating disorders such as tuberous sclerosis, which are caused by mutations in the TSC genes. The present invention further relates to methods and compositions for treating cancers mediated by TSC signaling disorders.

Accordingly, in some embodiments, the present invention provides a method of detecting increased S6 kinase activity in a subject, comprising providing a biological sample from a subject; and detecting increased S6 kinase activity in the biological sample. In some embodiments, detecting increased S6 kinase activity comprises a S6 kinase phosphatase assay. For example, in some embodiments, the S6 kinase phosphatase assay comprises hybridizing a phosphospecific antibody to a S6 kinase substrate. In certain embodiments, increased S6 kinase activity is indicative of an inactivated protein selected from the group consisting of TSC1 protein and TSC2 protein. In some embodiments, the inactivated protein is due to a mutation (e.g., a truncation) in a gene encoding said TSC1 protein or said TSC2 protein. In some embodiments, the present invention further comprises the step of providing a diagnosis to the subject based on said detecting increased S6 kinase activity. In some embodiments, the diagnosis is a diagnosis of tuberous sclerosis in said subject. In some embodiments, the present invention further comprises the step of providing treatment for tuberous sclerosis to said subject. In some embodiments, the treatment comprises administering a S6 kinase inhibitor to said subject. The present invention is not limited to a particular S6 kinase inhibitor. Any suitable S6 kinase inhibitor is contemplated including, but not limited to, rapamycin and rapamycin derivatives.

The present invention also provides a kit for the diagnosis of tuberous sclerosis, comprising reagents for detecting increased S6 kinase activity in a subject. In some embodiments, the reagents comprise a phosphospecific antibody specific for an S6 kinase substrate. In some embodiments, the kit further comprises instruction for using the reagents for diagnosing tuberous sclerosis in the subject. In certain embodiments, the instructions comprise instructions required by the United States Food and Drug Administration for use in in vitro diagnostic products.

The present invention further provides a method of treating tuberous sclerosis in a subject, comprising providing a subject diagnosed with tuberous sclerosis; and an inhibitor of S6 kinase; and administering the inhibitor to the subject. In some preferred embodiments, the administering results in a decrease in symptoms of tuberous sclerosis in the subject. The present invention is not limited to a particular S6 kinase inhibitor. Any suitable S6 kinase inhibitor is contemplated including, but not limited to, rapamycin and rapamycin derivatives.

In yet other embodiments, the present invention provides a method of screening compounds, comprising providing a cell expressing S6 kinase; and one or more test compounds; and screening the test compounds for the ability to inhibit the kinase activity of said S6 kinase. In some embodiments, screening the compounds for the ability to inhibit the kinase activity of S6 kinase activity comprises a S6 kinase phosphatase assay. In some embodiments, the S6 kinase phosphatase assay comprises hybridizing a phosphospecific antibody to a S6 kinase substrate. In some embodiments, the cell is in vitro. In some embodiments, the cell is a TSC2−/−cell. In other embodiments, the cell is in vivo. In some embodiments, the cell is in a non-human animal (e.g., a rat or a mouse). In some embodiments, the rat is an Eker rat. In some embodiments, the test compound is a drug. In some embodiments, the test compound is rapamycin. In other embodiments, the test compound is a derivative of rapamycin. The present invention further provides a drug identified by the method.

In other embodiments, the present invention provides a method of treating a disease, comprising providing a subject suffering from a disease, and an agent capable of reducing cellular energy levels, and administering the agent to the subject. In preferred embodiments, the disease comprises defective cells. In further embodiments, the defective cells comprise a defective TSC pathway. In even further embodiments, the method further provides co-administering rapamycin to the subject.

In preferred embodiments, the defective TSC pathway comprises a defective element of the TSC pathway such as TSC1, TSC2, Rheb, mTOR, S6K, and/or 4EBP-1.

In some preferred embodiments, the agent targets the defective cells. In other embodiments, the agent inhibits hexokinase. In other embodiments, the agent is 2-deoxyglucose. In other embodiments, the agent is the mitochondrial uncoupler FCCP. In other embodiments, the agent inhibits PKC. In other embodiments, the agent is Rottlerin. In even other embodiments, the agent is 5-aminoimidazole-4-carboxyamide ribonucleotide.

In other preferred embodiments, the disease is tuberous sclerosis. In other embodiments, the disease is cancer.

DESCRIPTION OF THE FIGURES

FIG. 1a shows that TSC1–TSC2 inhibits S6K kinase activity. HA-S6K was transfected in HEK293 cells in the presence or absence of TSC1–TSC2, as indicated. FIG. 1b shows that TSC1–TSC2 selectively inhibits phosphorylation of Thr 389, but not Thr 421/Ser 424 of S6K. FIG. 1c shows that TSC1–TSC2 does not inhibit Ras-induced activation of ERK. FIG. 1d shows the dose dependent inhibition of S6K phosphorylation on Thr 389 (left). TSC1–TSC2 has no effect on either basal or insulin-stimulated phosphorylation of Akt (right).

FIG. 2a shows enhancement of basal and stimulated phosphorylation of S6K by TSC2 RNA interference. FIG. 2b shows increased phosphorylation of endogenous S6K and S6 by TSC2 RNA interference. FIG. 2c shows that disease-derived TSC2 mutants are compromised in their ability to inhibit S6K.

FIG. 3a shows the Akt-dependent mobility shift of TSC2. FIG. 3b shows two-dimensional phosphopeptide mapping of in vivo $^{32}$P-labelled TSC2. FIG. 3c shows two-dimensional phosphopeptide mapping of HA–TSC2 in the presence of insulin (400 nM), LY294002 (50 M) or rapamycin (20 nM).

FIG. 4a shows a schematic representation of putative Akt phosphorylation sites in TSC2. The sites conserved in Drosophila dTsc2 are boxed. The TSC2 fragment 1 and fragment 2 regions used for the in vitro Akt phosphorylation assay are indicated. FIG. 4b shows mutational analysis of Akt phosphorylation sites. Mutants are indicated below each panel. Panel VIII is a schematic representation of the boxed region, denoting the specific phosphorylation sites altered by the corresponding alanine substitutions. Phosphopeptides that are missing in each mutant are indicated by open circles in panels I, II, IV and VI. FIG. 4c shows phosphorylation of recombinant TSC2 fragments by purified Akt. Two-dimensional phosphopeptide mapping of the in-vitro-phosphorylated TSC2 fragments is also shown (bottom).

FIG. 5a shows that substitution of phosphorylation sites by alanine increases TSC2 activity, whereas substitution with acidic residues decreases activity. FIG. 5b shows inhibition of 4E-BP1 phosphorylation by TSC2 mutants. FIG. 5c shows that acidic residue substitutions disrupt formation of the TSC1–TSC2 complex. FIG. 5d shows that the phosphomimetic mutant of TSC2 is unstable. The stability of TSC2 was determined in the presence of cycloheximide (300 M, 0–6h). FIG. 5e shows that the phosphomimetic TSC2 mutant is highly ubiquitinated.

FIG. 7a shows that the phosphorylation of Thr 389 of the S6K-dC104 mutant is not inhibited by rapamycin. FIG. 7b shows that TSC1–TSC2 does not inhibit Thr 389 phosphorylation of the S6K-dC104 mutant. FIG. 7c shows that TSC1–TSC2 does not inhibit insulin-induced S6K-dNC kinase activity. FIG. 7d shows that TSC1–TSC2 inhibits mTOR kinase activity. FIG. 7e shows that TSC1–TSC2 inhibits phosphorylation of mTOR. Cotransfection of TSC1–TSC2 inhibits phosphorylation of Ser 2448 on mTOR, as detected by immunoblotting with an anti-phospho-mTOR antibody (left). A reduction of endogenous TSC2 by RNAi-C increased phosphorylation of mTOR (right). FIG. 7f shows a proposed model for TSC1–TSC2 function in the regulation of cell growth.

FIG. 8a shows dephosphorylation of S6K and 4EBP1 by ATP depletion. FIG. 8b shows mobility shift of TSC2. FIG. 8c shows 2-DG-induces dephosphorylation of endogenous S6K, S6, 4EBP1, mTOR but not AKT. FIG. 8d shows 2-DG-induces phosphorylation of AMPK. FIG. 8e shows time course of 2-DG treatment. FIG. 8f shows 2-DG decreases intracellular ATP levels. FIG. 8g shows 2-DG increases the AMP/ATP ratio. FIG. 8h shows low glucose inhibits S6K.

FIG. 9a shows 2-DG stimulates the co-immunoprecipitation between endogenous TSC2 and AMPK. FIG. 9b shows reciprocal immunoprecipitation of endogenous TSC2 and AMPK. FIG. 9c shows expression levels of endogenous TSC1, TSC2, pAMPK and AMPK in HEK293 cells. FIG. 9d shows the C-terminal fragment of TSC2 interacts with endogenous AMPK.

FIG. 10a shows knockdown of TSC2 by RNA interference blocks the 2-DG response. FIG. 10b shows knockdown of TSC2 by RNA interference does not block rapamycin-induced dephosphorylation of S6K. FIG. 10c shows inhibition of S6K by AMPK overexpression is blocked by TSC2 RNAi. FIG. 10d shows knockdown of TSC2 has little effect on the 2-DG-induced phosphorylation of ACC and eEF2. FIG. 10e shows rapamycin has little effect on the 2-DG-induced phosphorylation of ACC and eEF2. FIG. 10f shows ATP depletion-induced dephosphorylation of S6K and 4EBP1 are compromised in TSC2−/−cells. FIG. 10g shows 2-DG induced 4EBP1 dephosphorylation is compromised in TSC2−/−cells.

FIG. 11a shows 2-DG induced TSC2 mobility shift is due to phosphorylation. FIG. 11b shows AMPK expression induces a slow migrating form of TSC2. HA–TSC1 and Myc-TSC2 were co-transfected with or without active AMPK αI subunit as indicated and blotted by anti-HA and anti-Myc antibodies, respectively. FIG. 11c shows an AMPK inhibitor blocks the 2-DG induced mobility shift of TSC2. AMPK inhibitor (Compound C, 10 μM) was added 30 minutes before the treatment of 2-DG as indicated. FIG. 11d shows kinase inactive AMPK mutant blocks 2-DG-induced dephosphorylation of S6K. HEK293 cells were transfected with increasing amounts of the kinase inactive AMPK mutant (AMPKDN). FIG. 11e shows AMPK inhibitor blocks the 2-DG induced dephosphorylation of S6K. FIG. 11f shows AMPK inhibitor partially blocks S6K dephosphorylation induced by glucose deprivation.

FIG. 12a shows 2-DG and AMPK induce TSC2 phosphorylation on multiple spots in vivo. FIG. 12b shows S1337 and S1341 are AMPK-dependent sites phosphorylated by 2-DG treatment. FIG. 12c shows AMPK directly phosphorylates TSC2 on S1345 but not S1337 or 1341 in vitro. FIG. 12d shows Ser1345 in TSC2 is phosphorylated in vivo. FIG. 12e shows T1227 in TSC2 is phosphorylated in vivo. FIG. 12f shows AMPK phosphorylates TSC2 on T1227 in vitro. FIG. 12g shows wild type TSC2 but not the S1337A/S1341A/S1345A mutant shows a mobility shift in response to 2-DG.

FIG. 13a shows mutation of the AMPK-dependent sites in TSC2 decreases TSC2 activity. FIG. 13b shows mutant TSC2 can form complex with TSC1. FIG. 13c shows cells expressing the AMPK phosphorylation mutant TSC2 (T1227A/S1345A) are less responsive to 2-DG treatment. FIG. 13d shows TSC2–3A mutant is less active to inhibit S6K. LEF (TSC2−/−epithelial) cells were infected with TSC2 retrovirus and selected for the neomycin resistant stable expressing cells. FIG. 13e shows the AMPK-dependent phosphorylation of TSC2 is important for glucose deprivation-induced S6K dephosphorylation.

FIG. 14a shows TSC2 but not TSC2–3A protects LEF cells from glucose deprivation-induced cell death. FIG. 14b shows glucose deprivation induces DNA fragmentation in vector and TSC2–3A but not in TSC2 expressing LEF cells. FIG. 14c shows glucose deprivation induces cleavage of caspase-3 and PARP in vector and TSC2–3A but not in TSC2 expressing LEF cells. FIG. 14d shows 2-DG decreases cell size in HEK293 cells. HEK293 cells were cultured in the presence of 12.5 mM 2-DG, TSC2 RNAi, or 20 nM rapamycin for 72 hours. FIG. 14e shows low glucose (2.8 mM) decreases cell size in HEK293 cells. FIG. 14f shows TSC2–3A is defective in cell size regulation. FIG. 14g shows a proposed model of TSC2 in cellular energy signaling pathway.

DEFINITIONS

Figure 1:
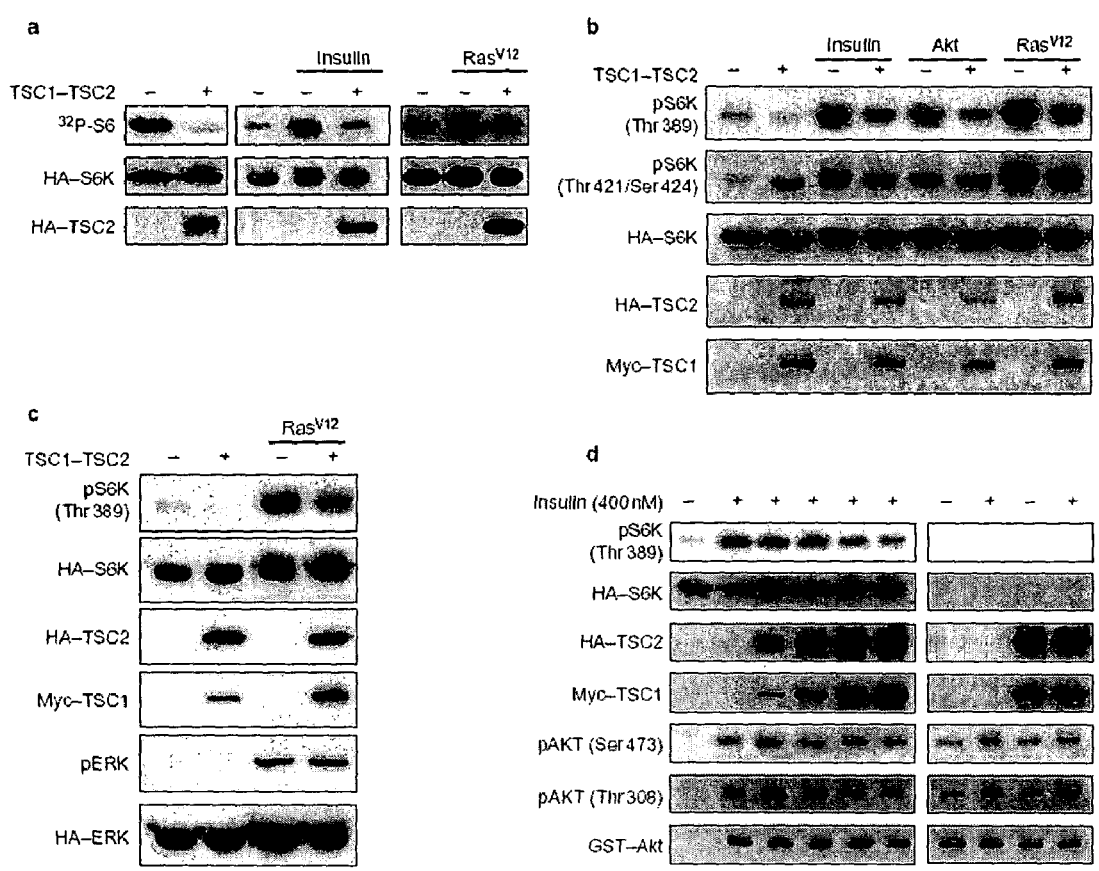
FIG. 1 shows inhibition of S6K by TSC1–TSC2.

To facilitate an understanding of the present invention, a number of terms and phrases are defined below:

As used herein, the terms "S6K" and "S6 kinase" are used interchangeably to refer to an S6K kinase (e.g., the human or non-human S6K kinase).

As used herein, the term "detecting increased S6 kinase activity in said biological sample" refers to detecting, using any suitable method, the presence of increased kinase activity of an S6 kinase relative to the level of kinase activity of a control sample (e.g., a control sample obtained from an individual known to have a normal level of S6 kinase activity). In some embodiments, kinase activity is assayed using the immunoassay described in the experimental section below. However, any assay that is capable of providing measure of kinase activity relative to a control may be utilized. In some embodiments, increased S6 kinase activity is indicative of an inactive TSC1 or TSC2 protein.

As used herein, the term "positive diagnosis of tuberous sclerosis in said subject" refers to a diagnosis of tuberous sclerosis in a subject. As used herein, the term "negative diagnosis of tuberous sclerosis in said subject" refers to the diagnosis of a subject of not having tuberous sclerosis.

As used herein, the term "TSC pathway" or "tuberous sclerosis complex pathway" refers generally to biological (e.g., molecular, genetic, cellular, biochemical, pharmaceutical, environmental) events (e.g., cellular pathways, cellular mechanisms, cellular cascades) involving the TSC-1 gene, the TSC-1 protein, the TSC-2 gene, and/or the TSC-2 protein. Examples of components of the TSC pathway include, but are not limited to, TSC-1, TSC-2, TSC-1/TSC-2, Rheb, mTOR, S6K, and 4EBP-1.

As used herein, the term "a subject with tuberous sclerosis" refers generally to a subject who has a defective TSC pathway. A defective TSC pathway may be identified by any recognized identification method (e.g., phenotypically, genetically, biochemically, and molecularly). One method for identifying subjects with tuberous sclerosis involves administration of a diagnostic assay to detect a defective TSC pathway (e.g., the diagnostic assay tests described heren).

As used herein, the term "a subject diagnosed with tuberous sclerosis" refers to a subject that has been medically determined (e.g., by a treating physician) as having tuberous sclerosis.

As used herein, the term "defective TSC pathway" or "sample having a defective TSC pathway" refers to samples demonstrated to have dysregulation (e.g., regulation of the pathway that results in a biological effect that causes adverse effects on a cell or tissue) within the TSC pathway (e.g., phenotypically, genetically, biochemically, and molecularly). One method of identifying a defective TSC pathway involves administration of a diagnostic assay to detect a defective TSC pathway (e.g., the diagnostic assay tests described herein).

As used herein, the term "reduces cellular energy levels" or "reduction of cellular energy levels" refers generally to a reduction (e.g., lowering, diminishing, lessening) of cellular glucose levels, amino acid levels, or ATP levels.

As used herein the term "said agent reduces cellular energy levels" or "methods of reducing cellular energy levels" refer generally to a targeting of cellular energy. Examples include, but are not limited to ATP and glucose. In addition, the term also refers generally to a targeting of components that assist in generating cellular energy. Examples include, but are not limited to, mitochondria, enzymes used to generate ATP (e.g., hexokinase), energy generating pathways (e.g., Krebs cycle), and drugs that regulate ATP metabolism (e.g., 2-deoxy-glucose).

As used herein, the term "hypertrophy" generally refers to the enlargement or overgrowth of an organ or body part due to an increase in size of its constituent cells. Examples include, but are not limited to, right ventricular hypertrophy, hypertrophic cardiomyopathy, and benign prostatic hypertrophy.

As used herein, the term "S6 kinase inhibitor" refers to a compound that inhibits the kinase activity of S6 kinase. In preferred embodiments, inhibitors inhibit the kinase activity to the level of kinase activity seen in a control sample. In particularly preferred embodiments, S6 kinase inhibitors reduce symptoms of diseases caused by increased S6 kinase activity (e.g., tuberous sclerosis).

The term "epitope" as used herein refers to that portion of an antigen that makes contact with a particular antibody.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "phosphospecific antibody" refers to an antibody that specifically binds to the phosphorylated form of a polypeptide (e.g., S6K) but does not specifically bind to the non-phosphorylated form of a polypeptide. In some embodiments, phosphospecific antibodies specifically bind to a polypeptide phoshphorylated at a specific position.

As used herein, the term "instructions for using said kit for detecting tuberous sclerosis in said subject" includes instructions for using the reagents contained in the kit for the detection and/or characterization of tuberous sclerosis in a biological sample from a subject. In some embodiments, the instructions further comprise the statement of intended use required by the U.S. Food and Drug Administration (FDA) in labeling analyte specific reagents (ASRs) or in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "providing a diagnosis to said subject based on said detecting increased S6 kinase activity" refers to providing a medical diagnosis (e.g., of tuberous sclerosis) based on the presence of increased S6 kinase activity in the subject.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

As used herein, the term "non-human animals" refers to all non-human animals including, but are not limited to, vertebrates such as rodents, non-human primates, ovines, bovines, ruminants, lagomorphs, porcines, caprines, equines, canines, felines, aves, etc.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50–90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 g/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31–9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39–7.52 [1989]).

The term "Western blot" refers to the analysis of protein (s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., tuberous sclerosis). Test compounds comprise both known and potential therapeutic compounds. A test compound can be determined to be therapeutic by screening using the screening methods of the present invention. In some embodiments of the present invention, test compounds include antisense compounds.

As used herein, the term "sample" is used in its broadest sense. In one sense, it is meant to include a specimen or culture obtained from any source, as well as biological and environmental samples. Biological samples may be obtained from animals (including humans) and encompass fluids (e.g., blood or urine), solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION

The present invention relates to compositions and methods for identifying abnormalities in TSC signaling pathways. In particular, the present invention relates to methods of diagnosing and treating disorders such as tuberous sclerosis, which are caused by mutations in the TSC genes. For example, in some embodiments, the present invention provides methods of diagnosing tuberous sclerosis by diagnosing increases in S6K kinase activity caused by mutations in the TSC1 or TSC2 genes. In other embodiments, the present invention provides methods of treating tuberous sclerosis by administering compounds that inhibit S6K kinase activity (e.g., rapamycin). The present invention further relates to methods and compositions for treating cancers mediated by TSC signaling disorders.

I. TSC1 and TSC2

TSC1 (also known as hamartin) encodes a protein with a relative molecular mass (Mr) of 130,000 (130K) that contains coiled-coil domains, but no obvious catalytic domains. TSC2 (also known as tuberin) encodes a 200K protein that contains a coiledcoil domain and a carboxy-terminal region, which shares homology to the Rap GTPase-activating protein (GAP)3. TSC2 has weak GAP activity towards Rap and Rab5. In mice, homozygous inactivation of either TSC1 or TSC2 is embryonic lethal, whereas heterozygous animals are prone to tumors (Onda et al., J. Clin.Invest. 104, 687–695 (1999); Au et al., Am. J. Hum. Genet. 62, 286–294 (1998); Kobayashi, T. et al., Proc. Natl Acad. Sci. USA 98, 8762–8767 (2001); each of which is herein incorporated by reference). In Drosophila melanogaster, inactivation of either dTsc1 or dTsc2 increases cell size and proliferation, whereas overexpression of dTsc1 and dTsc2 together, but not individually, decreases cell size, showing that Tsc1 and Tsc2 form a functional complex that regulates cell growth (Gao and Pan, Genes Dev. 15, 1383–1392 (2001); Ito et al., Cell 96, 529–539 (1999); Potter et al., Cell 105, 357–368 (2001); Tapon et al., Cell 105, 345–355 (2001); each of which is herein incorporated by reference). Furthermore, genetic analyses indicate that dTsc1 and dTsc2 function downstream of the insulin/insulin-like growth factor (IGF) receptor in the control of cell growth (Gao and Pan, supra; Potter et al., supra, Tapon et al., supra). It has been well established that components of the insulin pathway are important in cell growth (Kozma et al., Bioessays 24, 65–71 (2002); Stocker and Hafen, Curr. Opin. Genet. Dev. 10, 529–535 (2000); each of which is herein incorporated by reference). Members of this pathway include the positive regulators: insulin receptor (IR), insulin receptor substrate (IRS), phosphatidylinositol-3-OH kinase, (PI(3)K), PDK-1, Akt, TOR, S6K and eIF4E (eukaryote initiation factor 4E). Overexpression of these positive regulators increases cell size and/or number, whereas hypomorphic or null mutation of the positive regulators decreases cell number and size in Drosophila (Weinkove and Leevers, Curr. Opin. Genet. Dev. 10, 75–80 (2000); herein incorporated by reference). In mice, overexpression of constitutively active PI(3)K or Akt in the heart results in hypertrophy (Shioi, T. et al., EMBO J. 19, 2537–2548 (2000); Shioi, T. et al., Mol. Cell. Biol. 22, 2799–2809 (2002); each of which is herein incorporated by reference). Deletion of genes encoding IGFs or their receptors (DeChiara et al., Nature 345, 78–80 (1990); Liu et al., Cell 75, 59–72 (1993)), IRSs20 or S6K, results in dwarfism in mice (Shima et al., EMBO J. 17, 6649–6659 (1998); herein incorporated by reference), indicating the functional importance of these genes in the regulation of cell growth. Although the TSC1 and TSC2 tumor suppressor proteins have been shown to be involved in the regulation of proliferation and cell size, the precise function of the TSC1–TSC2 complex in the insulin signaling pathway has not been elucidated, nor has the molecular mechanism through which it functions as a tumor suppressor.

There are numerous genetic and epigenetic changes that result in increased PI(3)K signaling in human tumors (Vogt, Trends Mol. Med. 7, 482–484 (2001)). In humans, mutation of PTEN, which is a negative regulator of cell growth in insulin/IGF signaling pathways, results in excess activation of Akt, mTOR, S6K and eIF-4E, and causes several types of tumors, including hamartomas (Young and Povey, supra; Neshat, et al., Proc. Natl Acad. Sci. USA 98, 10314–10319 (2001); each of which is herein incorporated by reference). Among the positive components of insulin signaling, mTOR is essential for the control of cell growth and proliferation through the regulation of translation by S6Ks and 4E-BP1 (Schmelzle and Hall, Cell 103, 253–262 (2000); herein incorporated by reference). Phosphorylation of S6K and 4E-BP1 mediates the transduction of mitogen and nutrient signals to stimulate translation. The mRNAs encoding numerous ribosomal proteins and translation factors contain a 5' terminal oligopyrimidine tract (TOP). The TOP sequence confers selective translational induction in response to mitogenic stimulation. The translation of top mRNAs correlates with phosphorylation of the 40S ribosomal S6 protein by S6K (Shah et al., Am. J. Physiol. Endocrinol. Metab. 279, E715–E729 (2000); herein incorporated by reference). Hypophosphorylated 4E-BP1 binds to and inhibits eIF4E-dependent translation of CAP-containing mRNAs (Shah et al., supra). These eIF4E-regulated messages often encode proteins that are involved in proliferation, such as c-Myc and cyclin D1 (Sonenberg, and Gingras, *Curr. Opin. Cell Biol.* 10, 268–275 (1998); herein incorporated by reference). Activation of phosphorylation of S6K and inactivation of phosphorylation of 4E-BP1 correlates with PI(3)K-induced tumorigenesis (Neshat et al., PNAS 98, 10314 (2001); herein incorporated by reference). The importance of mTOR in tumorigenesis is supported by the fact that rapamycin inhibits tumor growth (Podsypanina, et al., *Proc. Natl Acad. Sci. USA* 98, 10320–10325 (2001); herein incorporated by reference).

Experiments conducted during the course of development of the present invention (See Experimental Section) demonstrated that TSC1–TSC2 inhibits the phosphorylation of S6K and 4E-BP1. The data show that TSC1–TSC2 exerts its effects through mTOR to regulate the activity of S6K and 4E-BP1. Further experiments demonstrated that the function of TSC1–TSC2 is negatively regulated by Akt-dependent phosphorylation in response to treatment with insulin and that the ability of TSC2 to inhibit S6K correlates with its tumor suppressor function.

Figure 2:
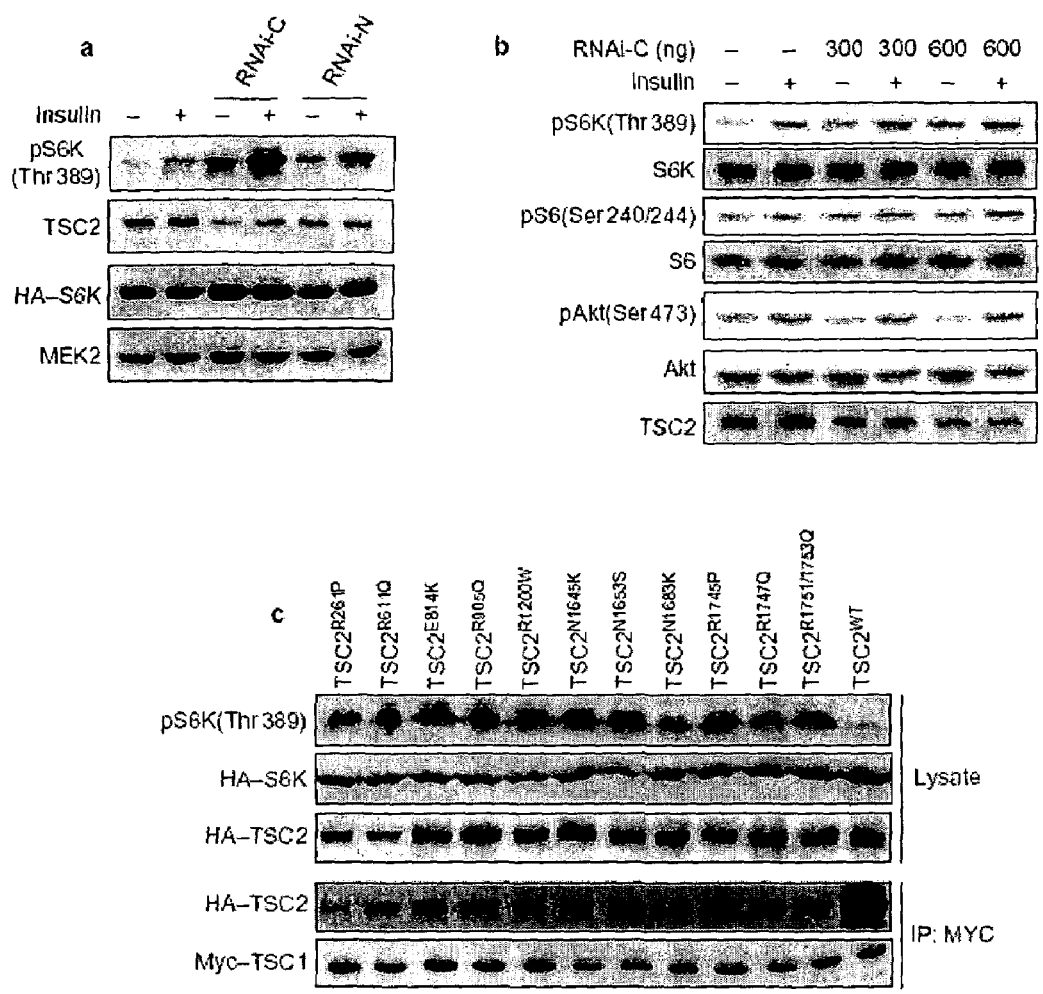
FIG. 2 shows the effects of endogenous TSC2 and disease-derived mutations on phosphorylation of S6K.
Figure 7:
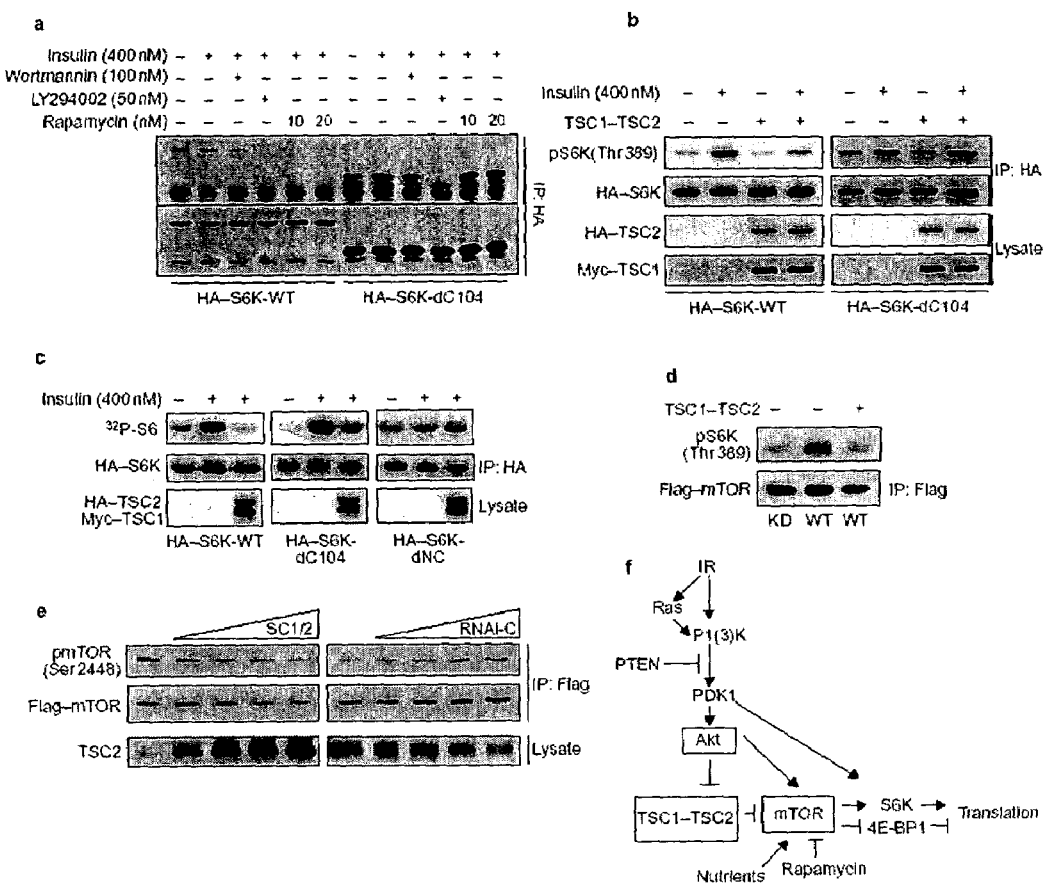
FIG. 7 shows that TSC1–TSC2 functions through mTOR to inhibit S6K.

Previous studies in mammalian cells have indicated that Akt promotes the activation of S6K (Aoki et al., *Proc. Natl Acad. Sci. USA* 98, 136–141 (2001); Burgering et al., *Nature* 376, 599–602 (1995); each of which is herein incorporated by reference). Activation of Akt by insulin or expression of a constitutively active Akt mutant results in increased S6K phosphorylation and kinase activity. The activation of S6K by Akt is an indirect process and may be mediated by mTOR (Scott et al., *Proc. Natl Acad. Sci. USA* 95, 7772–7777 (1998); Sekulic, A. et al. *Cancer Res.* 60, 3504–3513 (2000); each of which is herein incorporated by reference). The present invention is not limited to a particular mechanism. Indeed, an understanding of the mechanism is not necessary to practice the present invention. Nonetheless, it is contemplated that experiments conducted during the course of development of the present invention provide a possible mechanism for the regulation of S6K by Akt. In this model, TSC1–TSC2 functions downstream of Akt and upstream of mTOR to control S6K and 4E-BP1 activities in mammalian cells (FIG. 7f). It is further contemplated that one of the physiological functions of TSC1–TSC2 is to inhibit phosphorylation of S6K and 4E-BP1, which are key regulators of translation and cell growth (Dufner and Thomas, *Exp. Cell Res.* 253, 100–109 (1999); herein incorporated by reference). This activity of TSC1–TSC2 is important for their physiological functions because it is compromised by disease associated TSC2 mutations (FIG. 2c). Consistently, an enhancement of S6K phosphorylation has been observed in TSC1 null cells (Kwiatkowski et al. *Hum. Mol. Genet.* 11, 525–534; herein incorporated by reference). A functional assay for TSC1–TSC2 is currently not available, however, in some embodiments, the present invention provides an assay for inhibition and enhancement of S6K and 4E-BP1 phosphorylation, which provides a simple and relevant functional assay for TSC1–TSC2.

Genetic studies in Drosophila have examined the functions of TSC1–TSC2 in the regulation of cell growth. The present invention is not limited to a particular mechanism. Indeed, an understanding of the mechanism is not necessary to practice the present invention. Nonetheless, it is contemplated that TSC1–TSC2 is involved in the control of cell size and cell growth and that the TSC1–TSC2 signaling pathway provides a target for the inhibition of cell growth (e.g., in cancer).

Studies conducted during the course of development of the present invention show that Akt stimulates mTOR and, therefore, S6K activity by relieving the inhibition of TSC1–TSC2 (FIG. 7f). Activation of dS6K in Drosophila requires dPDK1, but not dPI(3)K and dAkt46. However, transgenic mouse models indicate a positive role for Akt in the activation of S6K and the control of cell size (Tuttle, et al. *Nature Med.* 7, 1133–1137 (2001); herein incorporated by reference). Experiments conducted during the course of development of the present invention indicate that Akt promotes activation of S6K. Phosphorylation of TSC2 by Akt affects its function through at least two mechanisms: first, phosphorylation decreases the activity of TSC2; second, phosphorylation destabilizes TSC2 protein. This destabilization is achieved by disrupting complex formation between TSC1 and TSC2 and inducing ubiquitination of the free TSC2. Derepression of TSC1–TSC2-mediated inhibition of mTOR is a possible mechanism of S6K activation by the insulin pathway. Experiments conducted during the course of development of the present invention show a molecular basis for how TSC1–TSC2 functions as tumor suppressor to inhibit cell growth and defines their role in insulin signaling. The major physiological functions of TSC1–TSC2 are inhibition of mTOR, S6K and 4E-BP1 activity.

The role of Akt and mTOR in insulin signaling is complex. Ser 2448 in mTOR has been shown to be a direct phosphorylation target of Akt40. Phosphorylation of Ser 2448 is stimulated by insulin (Scott et al., *Proc. Natl Acad. Sci. USA* 95, 7772–7777 (1998); herein incorporated by reference) and correlates with mTOR activity, but substitution of Ser 2448 by alanine does not affect the ability of mTOR to activate S6K42, indicating that the role of Akt in mTOR activation is more complex. However, this mutation was constructed in a rapamycin resistant mTOR mutant (containing an S2035I mutation), which has low activity towards 4E-BP1 (Reynolds et al., *J. Biol. Chem.* 277, 17657–17662 (2002); herein incorporated by reference). Therefore, such results are not adequate to exclude the importance of Ser 2448 phosphorylation in mTOR function. Indeed, recent studies further confirm the positive role of Ser 2448 phosphorylation in mTOR activation (Reynolds et al., supra). Phosphorylation of Ser 2448 in mTOR is enhanced by amino acid supplementation, supporting a role of Ser 2448 phosphorylation in mTOR activation (Reynolds et al, supra; Nave et al., *Biochem J.* 344, 427–431 (1999); herein incorporated by reference). Experiments conducted during the course of development of the present invention found that phosphorylation of Ser 2448 in mTOR is decreased by nutrient deprivation and increased by nutrient stimulation. Inhibition of S6K by rapamycin is mediated by the protein phosphatase PP2A49. Rapamycin treatment or amino-acid starvation activates PP2A-like activity towards S6K, and a weak association between PP2A and S6K has been detected (Peterson et al., *Proc. Natl Acad. Sci. USA* 96, 4438–4442 (1999); herein incorporated by reference). A positive function of mTOR in S6K activation has been established. Experiments conducted during the course of development of the present invention show that TSC1–TSC2 inhibits the kinase activity and phosphorylation of mTOR.

The present invention is not limited to a particular mechanism. Indeed, an understanding of the mechanism is not necessary to practice the present invention. Nonetheless, it is contemplated that rapamycin derivatives and other inhibitors of S6K find use as therapeutic agents for TSC and other disorders of cell growth (e.g., cancer).

Previous studies have indicated that phosphorylation of S6K and 4EBP1 by mTOR play an important role in the regulation of translation (Brown et al., *Nature* 377:441–446 (1995); Hara et al., *J. Biol. Chem.* 273:14484–94 (1998); Shah et al., *Am. J. Physiol. Endocrinol. Metab.*, 279: E715–729 (2000)). TSC1 or TSC2 mutant cells display elevated phosphorylation of both S6K and 4EBP1 (Goncharova et al., *J. Biol. Chem.* 277:30958–30967 (2002); Kenerson et al., Cancer Res. 62:5645–5650 (2002); Kwiatkowski et al., *Hum. Mol. Gen.* 11:525–534 (2002); Onda et al., *Mol. Cell Neurosci.* 21:561–574 (2002). In contrast, overexpression of TSC1 and TSC2 inhibits the phosphorylation of S6K and 4EBP1 (Goncharova et al., 2002; Inoki et al., *Nat. Cell Bio.* 4:648–657 (2002); Tee et al., *Proc. Natl. Acad. Sci.* 99:13571–13576 (2002). The present invention is not limited to a particular mechanism. Indeed, an understanding of the mechanism is not necessary to practice the present invention. Nonetheless, it is contemplated that one of the major cellular functions of TSC1/TSC2 is to inhibit translation by inhibiting the phosphorylation of S6K and 4EBP1.

The rate of translation is regulated by multiple signaling pathways including the availability of nutrients, growth factors, intracellular ATP levels, and environmental stresses (Browne and Proud, *Eur. J. Biochem.* 269:5360–5368 (2002); Proud, *Eur. J. Biochem.* 269:5338–5349 (2002). ATP depletion decreases S6K and 4EBP1 phosphorylation and inhibits translation. A previous study suggested that mTOR may mediate the ATP depletion signal because mTOR has a $K_m$ for ATP in the millimolar range which is comparable to physiological ATP levels (Dennis et al., *Genes Dev.* 16:1472–1487 (2001). However, normal cellular ATP levels do not drastically change under physiological energy starvation conditions. Instead, because cellular ATP concentration is much higher than the AMP concentration, a relatively small decrease in ATP levels will result in a relatively dramatic increase in AMP levels which is sensed by and stimulates the 5'AMP-activated protein kinase (AMPK) (Hardie et al., *Ann. Rev. Biochem.* 67:821–855 (1998). 2-Deoxy glucose (2-DG), a D-glucose analog, and 5-aminoimidazole-4-carboxyamide ribonucleotide (AICAR), activate AMPK (Corton et al., *Eur. J. Biochem.* 229:558–565 (1995). 2-DG and AICAR have been shown to increase phosphorylation of the eukaryotic elongation factor 2 (eEF2), indicating that AMPK plays a negative role in translation (Horman et al., *Curr. Bio.* 12:1419–1423 (2002). It has been also reported that both 2-DG and AICAR inhibit S6K activity (Kimura et al., *Genes Cells* 8:65–79 (2003); Krause et al., *Eur. J. Biochem.* 269:3751–3759 (2002). The mechanism of S6K inhibition by AMPK appears to go through the mTOR pathway (Kimura et al., 2003).

Figure 10:
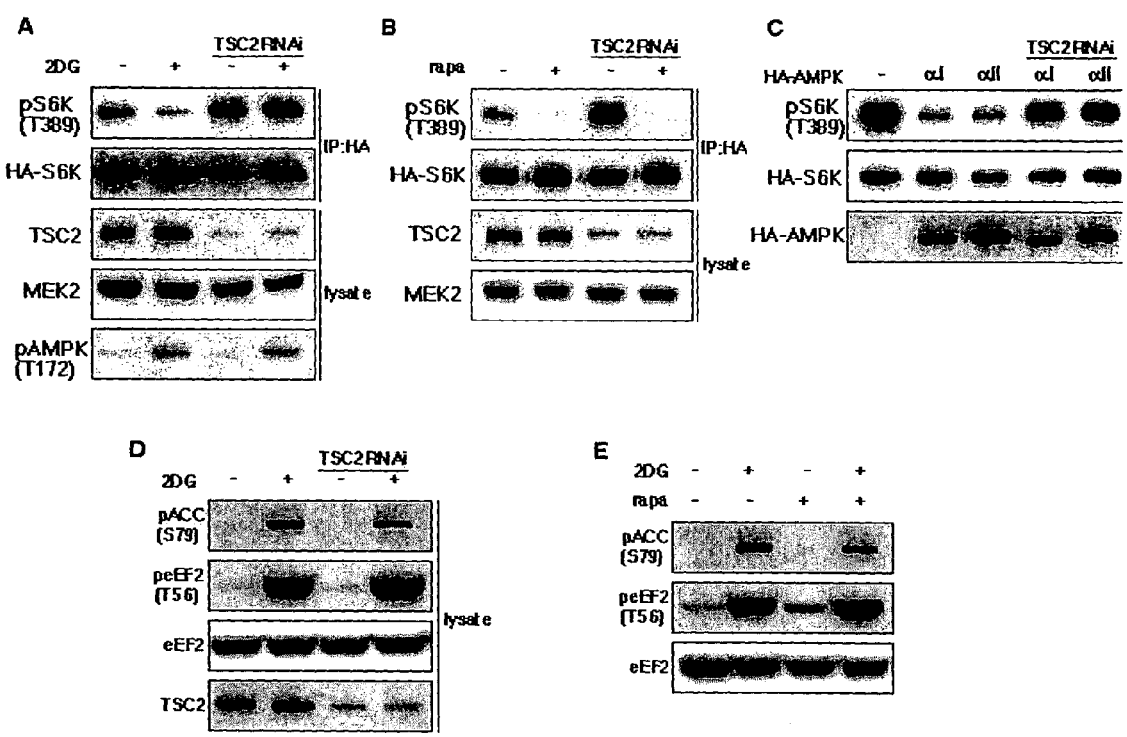
FIG. 10 shows TSC2 is required for 2-DG induced dephosphorylation of S6K.
Figure 10:
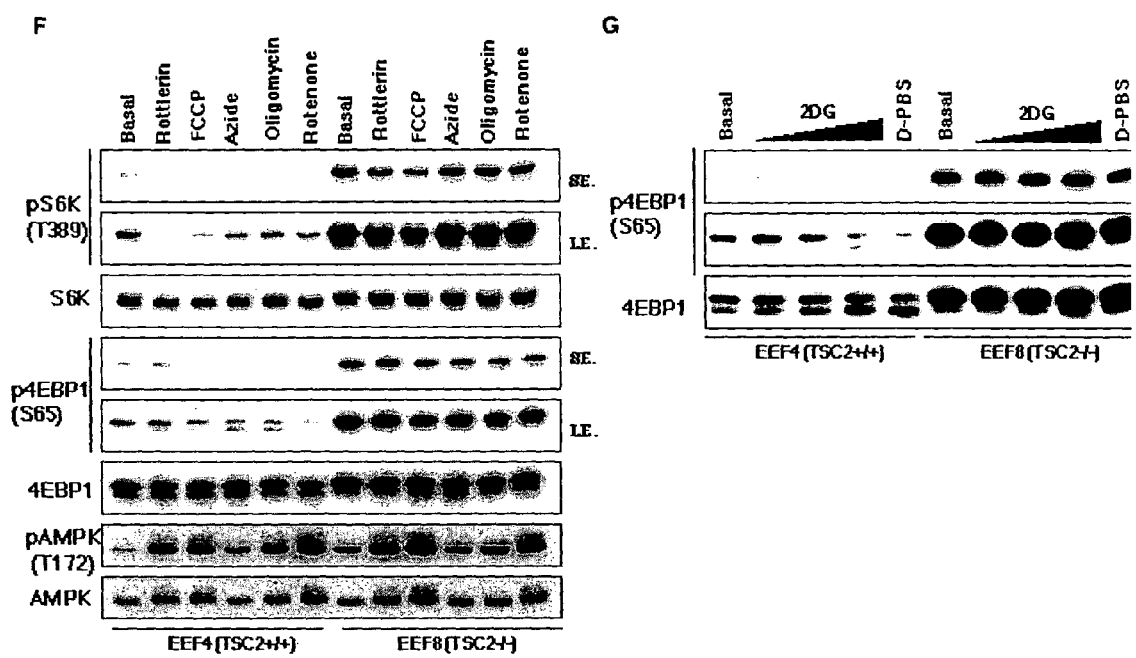
Figure 12:
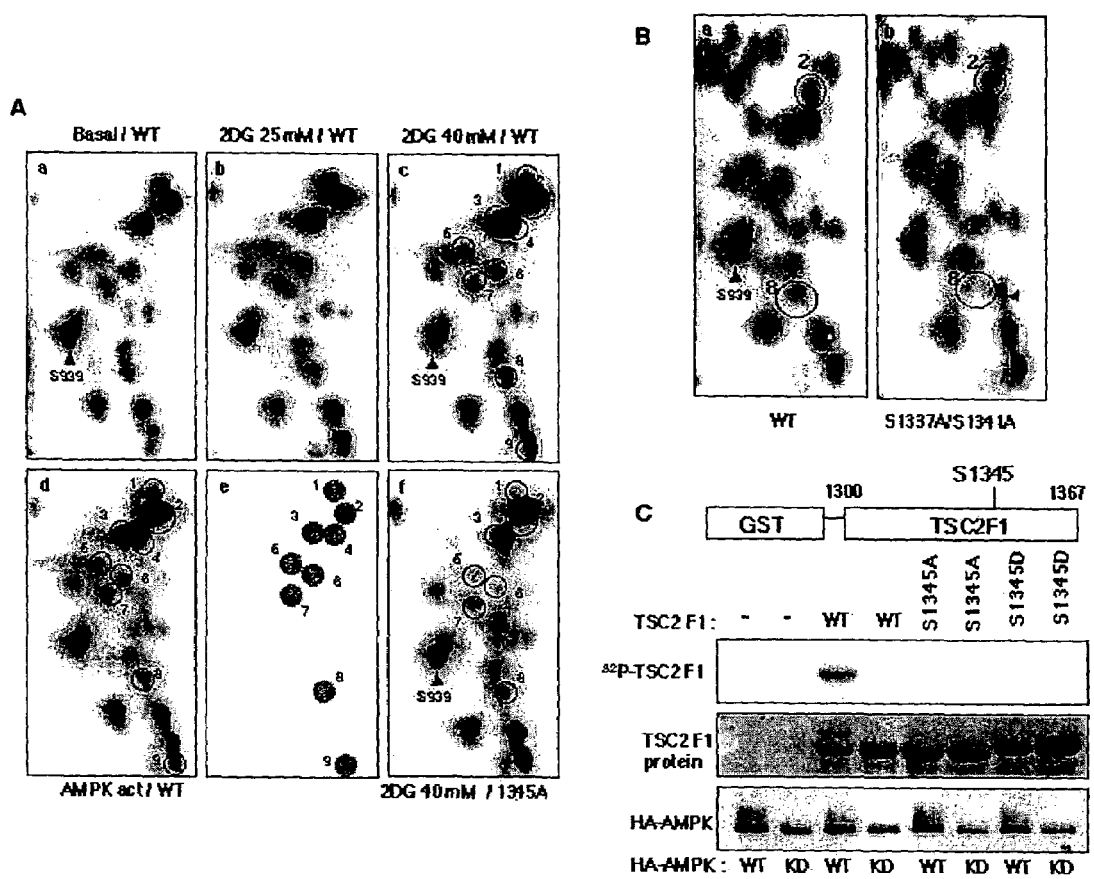
FIG. 12 shows AMPK phosphorylates TSC2 on S1227 and S1345.
Figure 12:
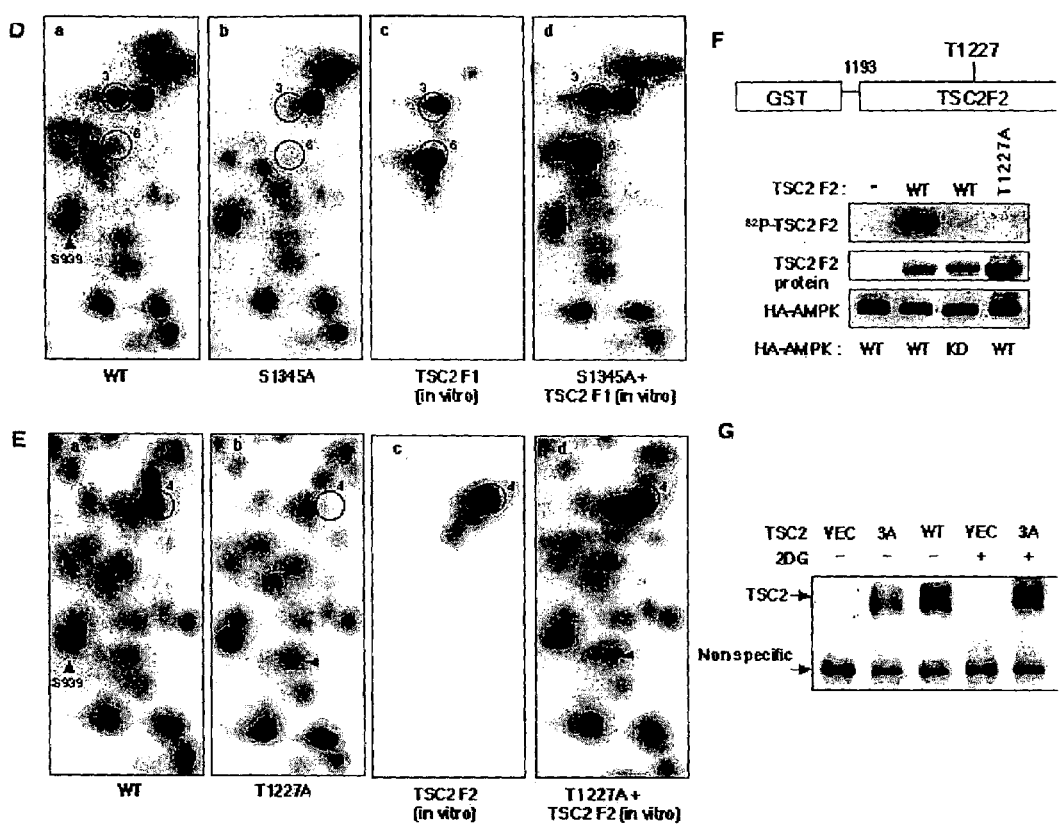
Figure 13:
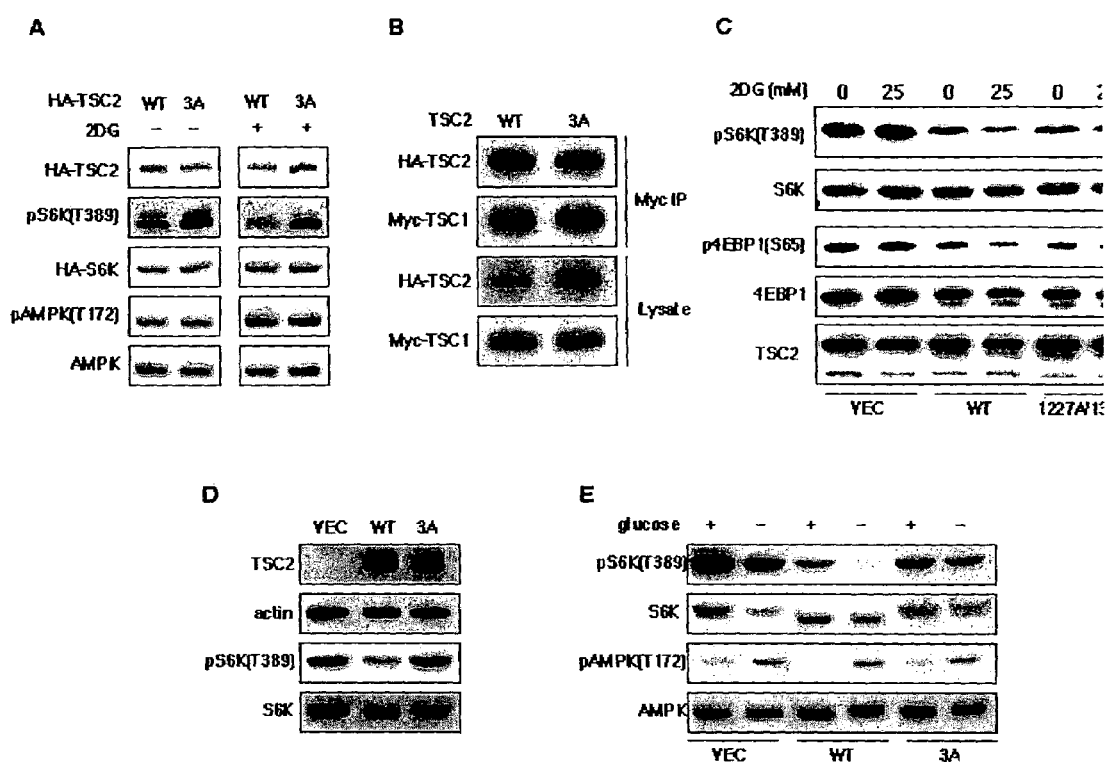
FIG. 13 shows AMPK phosphorylation is important for TSC2 function in the regulation of S6K phosphorylation in response to energy limitation.

Studies conducted during the course of development of the present invention show that TSC2 is regulated by cellular energy levels. Activation of AMPK by energy starvation results in direct phosphorylation of TSC2 on T1227 and S1345 (FIG. 12). Knockdown of TSC2 protein by RNA interference eliminates the ATP depletion-induced dephosphorylation of S6K (FIG. 10). Moreover, in response to energy starvation the TSC2-/-cells show a defective response in S6K dephosphorylation (FIG. 10). Furthermore, the energy depletion-induced dephosphorylation of S6K is restored by the expression of wild type TSC2, but not the AMPK phosphorylation mutant in TSC2-/-cells, demonstrating a critical function of TSC2 phosphorylation by AMPK in the regulation of translation by cellular energy starvation (FIG. 13).

The present invention is not limited to a particular mechanism. Indeed, an understanding of the mechanism is not necessary to practice the present invention. Nonetheless, it is contemplated that TSC2 plays an essential role to protect cells from glucose deprivation-induced apoptosis. AMPK-dependent phosphorylation of TSC2 is important for TSC2 function in cellular energy responses because expression of wild type TSC2, but not the AMPK phosphorylation mutant in TSC2-/-cells prevents apoptosis induced by glucose deprivation (FIG. 13). The present invention is not limited to a particular mechanism. Indeed, an understanding of the mechanism is not necessary to practice the present invention. Nonetheless, it is contemplated that an essential role of TSC2 and AMPK phosphorylation in the cellular energy response.

II. Diagnostic Applications

In some embodiments, the present invention provides methods of diagnosing TSC. Early diagnosis of TSC allows early intervention. For example, tumors can be identified and removed before they cause damage and pharmaceutical treatment (e.g., with a pharmaceutical of the present invention) can be started at an early time point.

In some embodiments, the present invention provides methods of diagnosing mutations in TSC1 or TSC2 directly. In other embodiments, the present invention provides methods of diagnosing mutations in TSC1 or TSC2 indirectly (e.g., through the diagnosis of increased S6K activity). The below description provides exemplary diagnostic screening methods. One skilled in the art recognizes that alternative diagnostic methods may be utilized.

A. Direct Detection

In some embodiments, the present invention provides methods of detecting mutations in TSC1 or TSC2 directly. Mutations in TSC1 and TSC2 are generally random. Most mutations result in a frameshift or premature stop codon. Thus, in some embodiments, mutant TSC1 or TSC2 genes are truncated.

1. Direct Detection

In some embodiments, mutations are detected by DNA sequencing of the TSC1 or TSC2 genes. In some embodiments, automated sequencing methods well known in the art are utilized. DNA sequencing is used to detect altered TSC1 or TSC2 nucleic acid sequences (e.g., containing frameshift or premature stop codons), thus diagnosing TSC.

2. Detection of Truncated TSC1 or TSC2 Proteins

In other embodiments, truncated TSC1 or TSC2 proteins are detected. Any suitable method may be used to detect truncated TSC1 or TSC2 proteins. For example, in some embodiments, cell-free translation methods from Ambergen, Inc. (Boston, Mass.) are utilized. Ambergen, Inc. has developed a method for the labeling, detection, quantitation, analysis and isolation of nascent proteins produced in a cell-free or cellular translation system without the use of radioactive amino acids or other radioactive labels. Markers are aminoacylated to tRNA molecules. Potential markers include native amino acids, non-native amino acids, amino acid analogs or derivatives, or chemical moieties. These markers are introduced into nascent proteins from the resulting misaminoacylated tRNAs during the translation process.

One application of Ambergen's protein labeling technology is the gel free truncation test (GFTT) assay (See e.g., U.S. Pat. No. 6,303,337, herein incorporated by reference). In some embodiments, this assay is used to screen for truncation mutations in a TSC1 or TSC2 protein. In the GFTT assay, a marker (e.g., a fluorophore) is introduced to the nascent protein during translation near the N-terminus of the protein. A second and different marker (e.g., a fluorophore with a different emission wavelength) is introduced to the nascent protein near the C-terminus of the protein. The protein is then separated from the translation system and the signal from the markers is measured. A comparison of the measurements from the N and C terminal signals provides information on the fraction of the molecules with C-terminal truncation (i.e., if the normalized signal from the C-terminal marker is 50% of the signal from the N-terminal marker, 50% of the molecules have a C-terminal truncation).

In still further embodiments, truncated proteins are detected by antibody binding. For example, in some embodiments, two antibodies are utilized. One antibody is designed (See e.g., below description of antibody generation) to recognize the C-terminus of TSC1 or TSC2 and a second antibody is designed to recognize the N-terminus of TSC1 or TSC2. Proteins that are recognized by the N-terminal, but not the C-terminal antibody are truncated. In some embodiments, quantitative immunoassays are used to determine the ratios of C-terminal to N-terminal antibody binding.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981, 785, 6,159,750, and 5,358,691, each of which is herein incorporated by reference. In some embodiments, the analysis and presentation of results is also automated. For example, in some embodiments, software that generates a prognosis based on the result of the immunoassay is utilized.

In other embodiments, the immunoassay described in U.S. Pat. Nos. 5,599,677 and 5,672,480; each of which is herein incorporated by reference.

B. Indirect Detection

In other embodiments, mutations in TSC1 or TSC2 are detected indirectly. Experiments conducted during the course of development of the present invention demonstrated that TSC1 and TSC2 inhibit S6K kinase activity (See Experimental Section). Mutations in TSC1 or TSC2 result in a increase in S6K kinase activity. In some embodiments, a increase in S6K kinase activity is assayed for using a phosph-S6K specific antibody (See FIG. 1 and 2 and the Experimental Section below). The present invention is not limited to a particular method of detecting S6K kinase activity. Any suitable method may be utilized, including those known in the art.

III. Antibodies

The present invention provides isolated antibodies or antibody fragments (e.g., FAB fragments). In preferred embodiments, the present invention provides monoclonal antibodies or fragments that specifically bind to an isolated polypeptide comprised of at least five amino acid residues of the proteins disclosed herein (e.g., TSC1, TSC2, S6K, mTOR, and Akt). These antibodies find use in the diagnostic and drug screening methods described herein.

An antibody against a protein of the present invention may be any monoclonal, polyclonal, or recombinant (e.g., chimeric, humanized, etc.) antibody, as long as it can recognize the protein. Antibodies can be produced by using a protein of the present invention as the antigen according to a conventional antibody or antiserum preparation process.

The present invention contemplates the use of monoclonal, recombinant, and polyclonal antibodies or fragments thereof. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]; herein incorporated by reference). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against an protein of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against a polypeptide of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

In other embodiments, the present invention contemplated recombinant antibodies or fragments thereof to the proteins of the present invention. Recombinant antibodies include, but are not limited to, humanized and chimeric antibodies. Methods for generating recombinant antibodies are known in the art (See e.g., U.S. Pat. Nos. 6,180,370 and 6,277,969 and "Monoclonal Antibodies" H. Zola, BIOS Scientific Publishers Limited 2000. Springer-Verlay New York, Inc., New York; each of which is herein incorporated by reference).

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a polypeptide of the present invention (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

IV. Drug Screening

In some embodiments, the present invention provides drug screening assays (e.g., to screen for drugs that inhibit the kinase activity of S6K). The present invention provides both in vitro (e.g., in cell culture) and in vivo (e.g., in animal models of TSC) to screen any number of candidate therapeutic compounds.

A. Candidate Compounds

The drug screening methods of the present invention utilize any number of candidate compounds useful in the treatment of TSC. In some embodiments, candidate compounds are rapamycin or rapamycin derivatives. Rapamycin is an antifungal antibiotic which is extractable from a streptomycete, e.g., Streptomyces hygroscopicus. Methods for the preparation of rapamycin are disclosed in Sehgal et al., U.S. Pat. Nos. 3,929,992, and 3,993,749, each of which is herein incorporated by reference. In addition, monoacyl and diacyl derivatives of rapamycin and methods for their preparation are disclosed in U.S. Pat. No. 4,316,885, herein incorporated by reference. U.S. Pat. No. 4,650,803 (herein incorporated by reference) discloses water soluble prodrugs of rapamycin, i.e., rapamycin derivatives including the following rapamycin prodrugs: glycinate prodrugs, propionate prodrugs and the pyrodlidino butyrate prodrugs. U.S. Pat. No. 5,118,678 (herein incorporated by reference) discloses carbamates of rapamycin. U.S. Pat. No. 5,100,883 (herein incorporated by reference) discloses fluorinated esters of rapamycin. U.S. Pat. No. 5,118,677 (herein incorporated by reference) discloses amide esters of rapamycin. U.S. Pat. No. 5,130,307 (herein incorporated by reference) discloses aminoesters of rapamycin. U.S. Pat. No. 5,117,203 (herein incorporated by reference) discloses sulfonates and sulfamates of rapamycin. U.S. Pat. No. 5,194,447 (herein incorporated by reference) discloses sulfonylcarbamates of rapamycin.

The drug screening methods of the present invention are not limited to rapamycin. Any number of candidate compounds may be utilized. In some embodiments, commercially available or known libraries of candidate compounds are screened. Preparation and screening of combinatorial chemical libraries is well known to those of skill in the art.

Such combinatorial chemical libraries include, but are not limited to, peptide libraries (see, e.g., U.S. Pat. No. 5,010, 175, Furka, Int. J. Pept. Prot. Res. 37:487–493 (1991) and Houghton et al., Nature 354:84–88 (1991); each of which is herein incorporated by reference). Other chemistries for generating chemical diversity libraries can also be used. Such chemistries include, but are not limited to: peptoids (PCT Publication No. WO 91/19735; herein incorporated by reference), encoded peptides (PCT Publication WO 93/20242; herein incorporated by reference), random biooligomers (PCT Publication No. WO 92/00091; herein incorporated by reference), benzodiazepines (U.S. Pat. No. 5,288,514; herein incorporated by reference), diversomers such as hydantoins, benzodiazepines and dipeptides (Hobbs et al., Proc. Nat. Acad. Sci. USA 90:6909–6913 (1993); each of which is herein incorporated by reference), vinylogous polypeptides (Hagihara et al., J. Amer. Chem. Soc. 114:6568 (1992); herein incorporated by reference), nonpeptidal peptidomimetics with -D-glucose scaffolding (Hirschmann et al., J. Amer. Chem. Soc. 114:9217–9218 (1992); herein incorporated by reference), analogous organic syntheses of small compound libraries (Chen et al., J. Amer. Chem. Soc. 116:2661 (1994); herein incorporated by reference), oligocarbamates (Cho et al., Science 261:1303 (1993); herein incorporated by reference), and/or peptidyl phosphonates (Campbell et al., J. Org. Chem. 59:658 (1994); herein incorporated by reference), nucleic acid libraries (see, Ausubel, Berger and Sambrook, all supra), peptide nucleic acid libraries (see, e.g., U.S. Pat. No. 5,539,083; herein incorporated by reference), antibody libraries (see, e.g., Vaughn et al., Nature Biotechnology, 14(3):309–314 (1996) and PCT/US96/10287; each of which is herein incorporated by reference), carbohydrate libraries (see, e.g., Liang et al., Science, 274:1520–1522 (1996) and U.S. Pat. No. 5,593, 853; each of which is herein incorporated by reference), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525, 735 and 5,519,134; morpholino compounds, U.S. Pat. No. 5,506,337; benzodiazepines, U.S. Pat. No. 5,288,514, and the like; each of which is herein incorporated by reference.

In other embodiments, libraries of compounds are spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145; herein incorporated by reference).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994]; each of which is herein incorporated by reference.

Libraries of compounds may be presented in solution (e.g., Houghten, Biotechniques 13:412–421 [1992]; herein incorporated by reference), or on beads (Lam, Nature 354: 82–84 [1991]), chips (Fodor, Nature 364:555–556 [1993]; each of which is herein incorporated by reference), bacteria or spores (U.S. Pat. No. 5,223,409; herein incorporated by reference), plasmids (Cull et al., Proc. Nad. Acad. Sci. USA 89:18651869 [1992]; herein incorporated by reference) or on phage (Scott and Smith, Science 249:386–390 [1990]; Devlin Science 249:404–406 [1990]; Cwirla et al., Proc. Natl. Acad. Sci. 87:6378–6382 [1990]; Felici, J. Mol. Biol. 222:301 [1991]; each of which is herein incorporated by reference).

B. In vitro Drug Screening

In some embodiments, the present invention provides in vitro drug screening assays. In some embodiments, the in vitro drug screening assays are cell culture assays. In one embodiment, the assay is a cell-based assay in which a cell that expresses a mutant TSC1 or TSC2 is contacted with a test compound, and the ability of the test compound to the modulate S6K activity is determined. Determining the ability of the test compound to modulate S6K activity can be accomplished using any suitable method, including, but not limited to, those disclosed herein. The cell, for example, can be of mammalian origin.

In other embodiments, a cell-free assay is provided in which a S6K or mTOR protein or biologically active portion thereof is contacted with a test compound and the ability of the test compound to alter activity of the S6K kinase activity or mTOR activity is evaluated. Cell-free assays involve preparing a reaction mixture of the target gene protein and the test compound under conditions and for a time sufficient to allow the two components to interact and bind, thus forming a complex that can be removed and/or detected.

In still further embodiments, cell lines (e.g., rodent or human cell lines such as TSC2–/–cell lines (e.g., LexF2 cells)) are treated with candidate compounds and these cell lines are evaluated for their ability to induce tumors in nude mice (See e.g., U.S. Pat. No. 6,235,873, herein incorporated by reference). For example, in some embodiments, the ability of cell lines treated with candidate compounds to induce tumors is compared with the ability of control cell lines not treated with the candidate compounds.

C. In vivo Drug Screening

In other embodiments, in vivo drug screening methods are utilized. In some embodiments, the Ecker rat, which serves as an animal model for TSC, is utilized (available from, e.g., Fox Chase Cancer Center, Philadelphia, Pa.). In other embodiments, a mouse model of TSC (See e.g., Kwiatkowski et al., Hum Mol Genet 2002 Mar 1;11(5):525–34; herein incorporated by reference) is utilized. Animal models are administered candidate compounds and the effect of the candidate compounds on symptoms of TSC is observed. Preferred compounds are those that reduce or eliminate symptoms of TSC, but do not cause other adverse effects to the animals. Animal models (such as those described herein) are further utilized to determine the efficacy, toxicity, side effects, or mechanism of action, of treatment with such an agent. Furthermore, novel agents identified by the above-described screening assays can be, e.g., used for treatments as described herein.

V. Therapies

In some embodiments, the present invention provides therapies for the treatment of TSC. In other embodiments, the present invention provides therapies for the treatment of cancer.

A. TSC Therapies

In some embodiments, the present invention provides methods of treating TSC. In some embodiments, the methods comprise administering inhibitors of S6K or mTOR (e.g., compounds identified in the drug screening assays described above). In some embodiments, the treatment comprises the administration of rapamycin or rapamycin derivatives or other therapeutic compounds identified using the above described drug screening methods. In still other embodiments, the TSC therapies comprise genetic therapies (e.g., gene therapy). In still further embodiments, the treatments comprise antibody therapy (e.g., humanized antibody therapy).

1. Drug Therapies

In some embodiments, small molecule therapeutics identified using the above-described drug screening methods are utilized as TSC therapeutics. Compounds are preferably formulated as pharmaceutical compounds (e.g., as described below). Dosages are determined, e.g., using the methods described below. One skilled in the relevant arts knows well how to formulate, determine dosages, and administer therapeutic compounds of the present invention. 2. Genetic Therapies The present invention contemplates the use of any genetic manipulation for use in modulating the expression of TSC1 and TSC2. For example, in some embodiments, the genetic therapies comprise the administration of wild type versions or TSC1 or TSC2 to a subject. Delivery of nucleic acid construct to cells in vitro or in vivo may be conducted using any suitable method. A suitable method is one that introduces the nucleic acid construct into the cell such that the desired event occurs (e.g., expression of the wild type TSC1 or TSC2 gene).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. patent application Ser. Nos. 6,033,908, 6,019,978, 6,001, 557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

3. Antibody Therapies

In some embodiments, the present invention provides methods of inhibiting S6K or mTOR using antibody therapies. Preferred antibodies are those that reduce symptoms of TSC (e.g., by inhibiting the signaling functions of S6K or mTOR). Preferred antibodies against S6K are antibodies that inhibit the kinase activity of S6K. Any suitable antibody (e.g., monoclonal, polyclonal, or synthetic) may be utilized in the therapeutic methods disclosed herein. In preferred embodiments, the antibodies used for cancer therapy are humanized antibodies. Methods for humanizing antibodies are well known in the art (See e.g., above descriptions and U.S. Pat. Nos. 6,180,370, 5,585,089, 6,054,297, and 5,565, 332; each of which is herein incorporated by reference). In preferred embodiments, antibody based therapeutics are formulated as pharmaceutical compositions as described below.

B. Cancer Therapies

The present invention is not limited to the treatment of TSC. As described above, it is further contemplated that rapamycin and rapamycin derivatives (e.g., those described above) find use in the treatment of a variety of cancers. Rapamycin and derivatives can be screened for their ability to reduce tumor growth using any suitable screening method (e.g., those described above). For example, in some embodiments, animal models of cancer are treated with rapamycin. In other embodiments, nude mice with tumors or cancer cell lines are utilized for drug screening. The present invention is not limited to the use of rapamycin as a cancer therapeutic. As described above, it is contemplated that compounds that inhibit mTOR and S6K signaling find use as cancer therapeutics.

C. Pharmaceutical Compositions

The present invention further provides pharmaceutical compositions (e.g., comprising the pharmaceutical compounds described above). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Certain embodiments of the invention provide pharmaceutical compositions containing (a) one or more of the compounds of the present invention and (b) one or more other chemotherapeutic agents. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Other chemotherapeutic agents are also within the scope of this invention. Two or more combined compounds may be used together or sequentially.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 µg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 µg to 100 g per kg of body weight, once or more daily, to once every 20 years.

VI. Discussion

Protein synthesis is a major cellular process regulated by a wide array of intracellular and extracellular conditions such as mitogenic growth factors, amino acid concentrations, and cellular energy levels (Schmidt, *Oncogene* 18:2988–2996 (1999). One of the major controls of translation is mediated by the phosphorylation of S6K and 4EBP1 by mTOR (Proud, 2002). Studies conducted during the course of development of the present invention demonstrated that TSC2 plays a major physiological role in response to cellular energy level (FIG. 7G). The present invention is not limited to a particular mechanism. Indeed, an understanding of the mechanism is not necessary to practice the present invention. Nonetheless, it is contemplated that phosphorylation of TSC2 by Akt relays the growth factor signals and suppresses the ability of TSC2 to inhibit S6K and 4EBP1 phosphorylation. In contrast, phosphorylation of TSC2 by AMPK initiated by low energy cellular levels stimulates TSC2 activity. These results demonstrate that the AMPK-dependent phosphorylation of TSC2 is required for ATP depletion-induced dephosphorylation of S6K.

Protein synthesis utilizes approximately 25–30% of the total cellular energy and must be tightly coordinated with cellular energy status. Inhibition of translation may represent a major physiological response in cells under energy limitation. The present invention is not limited to a particular mechanism. Indeed, an understanding of the mechanism is not necessary to practice the present invention. Nonetheless, a mechanism is presented in FIG. 7G. Based on the model presented in FIG. 7G, mTOR is in the energy sensing pathway downstream of TSC1/TSC2. However, AMPK is likely the cellular energy sensor and functions upstream of TSC1/TSC2. AMPK can inhibit translation by at least two mechanisms, one by phosphorylation of the eukaryotic elongation factor 2 (eEF2) (Horman et al., 2002) and the other by phosphorylation of TSC2. However, phosphorylation of eEF2 by AMPK is not dependent on the TSC-mTOR pathway. The present invention is not limited to a particular mechanism. Indeed, an understanding of the mechanism is not necessary to practice the present invention. Nonetheless, it is contemplated that activation of AMPK plays a major role in the inhibition of protein synthesis by suppressing the functions of multiple translation regulators including S6K, 4EBP1, and eEF2 in response to energy starvation and low metabolic conditions. TSC2 is a key downstream target of AMPK.

Glucose deprivation induces massive apoptosis in TSC2−/−LEF cells. Expression of wild type TSC2 completely blocks apoptosis while expression of the TSC2–3A mutant fails to protect cells from apoptosis. Moreover, TSC2 only protects from the glucose deprivation but not DNA damage-induced apoptosis. The present invention is not limited to a particular mechanism. Indeed, an understanding of the mechanism is not necessary to practice the present invention. Nonetheless, it is contemplated that TSC2 plays an essential and specific role in the cellular energy response. The function of TSC2 in the cellular energy response is further supported by the fact that energy limitation by glucose deprivation or 2-DG treatment also decreases cell size. In addition, TSC2 expression also reduces cell size. The present invention is not limited to a particular mechanism. Indeed, an understanding of the mechanism is not necessary to practice the present invention. Nonetheless, it is contemplated that energy limitation and TSC2 similarly regulate size of cultured mammalian cells. This study also establishes the importance of TSC2 phosphorylation by AMPK in the physiological response to cellular energy limitation. It is contemplated that the activation of TSC2 by AMPK-dependent phosphorylation results in a decrease of protein synthesis and conservation of cellular energy (FIG. 7G). Consistent with this model, rapamycin significantly protects LEF cells from glucose deprivation-induced apoptosis (unpublished data). The inability of TSC2−/−cells to suppress translation under the energy starvation condition could produce the detrimental effects and trigger apoptosis. The present invention reveals an important physiological function of TSC2 in cell growth and cell survival. In some embodiments, it is contemplated that any method (e.g., reduction in supply of glucose or amino acids, drugs that regulate ATP metabolism, etc.) of reducing cellular energy levels finds use in the therapeutic methods of the present invention.

It is interesting to note that mutations in AMPK have been implicated in familial hypertrophic cardiomyopathy (Hardie and Hawley, 2001). Furthermore, inhibition of mTOR by rapamycin has been a well documented in the suppression of cardiac hypertrophy (Shioi et al., *Circulation* 107:1664–1670 (2003). TSC2 is a prominent negative regulator of cell size control in Drosophila (Potter and Xu, *Curr. Opin. Genet. Dev.* 11:279–286 (2001) and in mammalian cells from this study. All these observations are consistent with the non-limiting model that TSC2 acts downstream of AMPK to inhibit mTOR. This provides a use of TSC2 in mediating the function of AMPK in cardiac hypertrophy.

In conclusion, the tumor suppressor TSC2 integrates signals from multiple pathways to regulate translation, cell size, and apoptosis. TSC2 is involved in the cellular response to metabolic status and energy levels. Activation of TSC2 by AMPK-dependent phosphorylation prepares cells for an unfavorable growth environment and results in protection from cell death. In addition to causing tuberous sclerosis, inactivation of the TSC1/TSC2 tumor suppressor complex has a role in oncogenic pathways and cellular hypertrophy. The present invention provides methods for depletion of cellular energy levels that selectively kill TSC1 or TSC2 minus cancer cells and, therefore, provide a therapeutic treatment for cancers and other conditions.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); and ° C. (degrees Centigrade).

A. Methods

Antibodies, Plasmids and Reagents

Anti-S6K, anti-phospho S6K, anti-mTOR, anti-phospho mTOR, anti-Akt, anti-phospho Akt, antiphospho 4EBP-1 and anti-phospho ERK antibodies were from Cell Signalling Inc. Anti-TSC2 and anti-Myc antibodies were from Santa Cruz Biotechnology (Santa Cruz, Calif.). Anti-HA and anti-Flag antibodies were from Covance (Princeton, N.J.) and Sigma (St Louis, Mo.), respectively. HA-tagged S6K1 (II) and GST-S6 constructs were obtained from J. Blenis (Columbia Univ., NY, N.Y.). Flag-tagged mTOR and kinase-inactive mTOR were obtained from S. Schreiber (Harvard Univ, Cambridge, Mass.). All other DNA constructs, including H-RasV12, PTEN, PTEN-CS, Akt, Akt-KM, Flag-ubiquitin and Flag-4E-BP1, were laboratory stock. All mutant constructs of TSC2 were created by PCR mutagenesis and verified by DNA sequencing. LY294002 was from Calbiochem (San Diego, Calif.); phosphatase was from New England Biolabs (Beverly, Mass.). MG132 was from the Peptide Institute. Cycloheximide and wortmannin were from Sigma. D-PBS was from Gibco. Rapamycin was from Cell Signalling.

Cell Culture, Transfection and Immunoprecipitation

HEK293 cells were seeded and maintained in Dulbecco's modified Eagle's medium (DMEM) containing 10% fetal bovine serum (FBS). Transfection was performed in serum-free conditions using Lipofectamine reagent (Invitrogen, Carlsbad, Calif.) in accordance with the manufacturer's instructions. In brief, 4 h after transfection, the cells were recovered in DMEM containing 10% FBS for 16 h and then starved for 16–24 h. Cells were then lysed in lysis buffer (10 mM Tris-HCl at pH 7.5, 100 mM sodium chloride, 1% NP-40, 1% Triton X-100, 50 mM sodium fluoride, 2 mM EDTA, 1 mM phenyl methylsulphonyl fluoride, 10 g ml$^{-1}$ leupeptin and 10 g ml$^{-1}$ aprotinine) and immunoprecipitated with the indicated antibodies and protein G-Sepharose beads. Immunocomplexes were analyzed by SDS-polyacrylamide gel electrophoresis (PAGE).

Kinase Assay

For the S6K assays, HEK293 cells grown in six-well plates were transfected with 10–20 ng HA-S6K constructs, with or without various plasmids, as indicated in the figures. HA-S6K was immunoprecipitated from serum-starved cells with an anti-HA antibody and analyzed by in vitro kinase assay using purified GST-S6 as a substrate (Pearson et al., *EMBO J.* 14, 5279–5287 (1995)).

For the Akt kinase assays, 10 g of GST-Akt or GST-Akt-KM (kinase inactive) DNA was transfected into HEK293 cells in 10 cm plates in the presence of 2 g RasV12. GST-Akt was purified and used to phosphorylate 5 g of purified GST-TSC2 fragment 1 (amino acids 910–1112) or fragment 2 (amino acids 1357–1765) in vitro. mTOR kinase assays were performed as previously described (Dennis et al,. *Science* 294, 1102–1105 (2001)). Briefly, HEK293 cells were transiently transfected with Flag-mTOR, with or without TSC1-TSC2. The cells were lysed and immunoprecipitated with an anti-Flag antibody and analyzed by in vitro kinase assay using purified GST-S6K as a substrate. The mTOR kinase buffer contained 2 mM ATP. Phosphorylation of GST-S6K was determined by immunoblot analysis with an anti-phospho-Thr 389 S6K antibody.

RNA Interference

RNAi-N and RNAi-C represent double-stranded RNA oligonucleotides corresponding to amino acid residues 164–170 (RNAi-N) and 1518–1524 (RNAi-C) of TSC2 (Elbashir et al. *Nature* 411, 494–498 (2001)). HEK293 cells were transfected with 200–1000 ng RNAi with or without indicated plasmids using Lipofectamine reagent, as described above. The level of endogenous TSC2 was determined by immunoblotting with an anti-TSC2 antibody.

Metabolic Labeling and Two-dimensional Phosphopeptide Mapping

HEK293 cells were cotransfected with HA-tagged TSC2, Myc-tagged TSC1 and the indicated plasmids. Cells were phosphate- and serum-starved for 4 h before incubation with 0.25 mCi ml$^{-1}$ 32P-orthophosphate (ICN) for 4 h.

Cells were washed once with ice-cold PBS and lysed. HA-tagged TSC2 was immunoprecipitated, resolved by SDS-PAGE and transferred to a PVDF membrane. Phosphorylated TSC2 was visualized by autoradiography and phosphopeptide mapping was then performed. In brief, the phosphorylated TSC2 bands were excised, fixed in methanol and incubated in 500 1 of 0.5% polyvinylpyrrolidone-40 dissolved in 100 mM acetic acid for 30 min at 37° C. The sample were then digested with 20 g of TPCK-treated trypsin (Sigma) at 37° C. in 75 mM ammonium bicarbonate buffer at pH 8.0 containing 5% acetonitrile. After digestion, samples were dried under vacuum and suspended in 10 1 of water. Samples were spotted onto a cellulose plate and first dimensional electrophoresis was performed using 1% ammonium bicarbonate buffer at pH 8.9. The plates were separated by chromatography in the second dimension in chromatography buffer (n-butanol:pyridine:acetic acid:water; 20:24:6:30). The plates were dried and phosphopeptides were visualized by autoradiography.

B. Results

The Effect of TSC1–TSC2 on S6K Activity

To elucidate a mechanism of TSC1–TSC2 function in the control of cell growth, the effect of TSC1–TSC2 on S6K activity in mammalian cells was examined. Co-expression of TSC1 and TSC2 inhibited basal S6K kinase activity, in addition to and insulin- and Ras-stimulated S6K kinase activity (FIG. 1a). This inhibitory activity of TSC1–TSC2 is consistent with its negative role in cell growth control. S6K activity is activated by phosphorylation on several residues, including Thr 389, Thr 421 and Ser 424 (Dufner and Thomas, *Exp. Cell Res.* 253, 100–109 (1999)). Phosphorylation of these residues was stimulated by insulin, Akt and activated Ras (FIG. 1b). Furthermore, co-expression of TSC1–TSC2 inhibited phosphorylation of Thr 389 under all three conditions (FIG. 1b). Thr 389 is a known rapamycin-sensitive phosphorylation site that correlates with activation of S6K[29]. Co-expression of TSC1–TSC2 had little effect on the phosphorylation of Thr 421 or Ser 424 in S6K (FIG. 1b), which are rapamycin-insensitive sites (Dufner et al., supra). The present invention is not limited to a particular mechanism. Indeed, an understanding of the mechanism is not necessary to practice the present invention. Nonetheless, it is contemplated that these results show that the TSC1–TSC2 complex may exert its effects through mTOR.

To test the specificity of TSC1–TSC2 in S6K activation, the effect of TSC1–TSC2 on ERK, which is also activated by Ras, was examined. The results showed that overexpression of TSC1–TSC2 had no effect on Ras-induced phosphorylation of ERK, whereas phosphorylation of S6K was inhibited in the same experiment (FIG. 1c). These observations demonstrate that TSC1–TSC2 specifically inhibits the phosphorylation and activation of S6K.

To determine the position of TSC1–TSC2 in the insulin pathway, the effect of TSC1–TSC2 overexpression on insulin-induced phosphorylation of Akt, which is upstream of mTOR and S6K, was examined. The results demonstrate that TSC1–TSC2 is unable to inhibit the insulin-induced phosphorylation of Akt but does inhibit phosphorylation of S6K in a dose dependent manner (FIG. 1d). The present invention is not limited to a particular mechanism. Indeed, an understanding of the mechanism is not necessary to practice the present invention. Nonetheless, it is contemplated that TSC1–TSC2 functions downstream of, or parallel to, Akt.

RNA Interference

RNA interference (RNAi) was used to test the effect of endogenous TSC2 on S6K. Two RNA duplexes, corresponding to either an amino-terminal (RNAi-N) or C-terminal (RNAi-C) region of TSC2, were used to suppress expression of endogenous TSC2 (FIG. 2a). Transfection of RNAi-C or RNAi-N caused a significant reduction of endogenous TSC2 protein levels in HEK293 cells, whereas TSC2 RNAi had no effect on expression levels of MEK2. The data demonstrate that a reduction of endogenous TSC2 protein levels by TSC2 RNAi increases both basal and insulin-stimulated phosphorylation of the transfected S6K (FIG. 2a). Control experiments with unrelated RNA oligonucleotides had no effect on the phosphorylation of S6K. The effect of TSC2 RNAi on the phosphorylation of endogenous Akt, S6K and S6 was also examined. Transfection of TSC2 RNAi induced a small but reproducible increase in the phosphorylation of both endogenous S6K and S6, but not of Akt (FIG. 2b). An increase of S6 phosphorylation indicates that the TSC2 RNAi enhances S6K activity. Compared with cotransfected haemagglutinin (HA)-tagged S6K, the increase in phosphorylation of endogenous S6K is less dramatic. This is because the transfection efficiency is less than 100%. Endogenous S6K in untransfected cells diluted the effect of RNAi in transfected cells. Therefore, the real increase in endogenous S6K in cells transfected with TSC2 RNAi should be more dramatic than the data shown in FIG. 2b. The above observations demonstrate that one physiological function of TSC1-TSC2 is to inhibit the phosphorylation and activation of S6K kinase.

Effect of TSC Mutations on Kinase Activity

Many mutations in TSC1 and TSC2 have previously been identified in patients (Dabora et al. *Am. J. Hum. Genet.* 68, 64–80 (2001); Jones et al., *Am. J. Hum. Genet.* 64, 1305–1315 (1999); herein incorporated by reference). The effect of these disease-derived mutations on the ability of TSC2 to inhibit S6K activity was next tested. Specifically, point mutations of hydrophilic or charged residues were tested, because mutation of surface residues is less likely to affect the tertiary structure of TSC2. Among eleven disease-associated mutants analyzed, all showed a decrease in ability to inhibit S6K phosphorylation, compared with the wild-type control (FIG. 2c). The present invention is not limited to a particular mechanism. Indeed, an understanding of the mechanism is not necessary to practice the present invention. Nonetheless, it is contemplated that these data show that the inhibition of S6K activity by TSC1–TSC2 is physiologically relevant.

Phosphorylation of TSC2 by Akt

Figure 3:
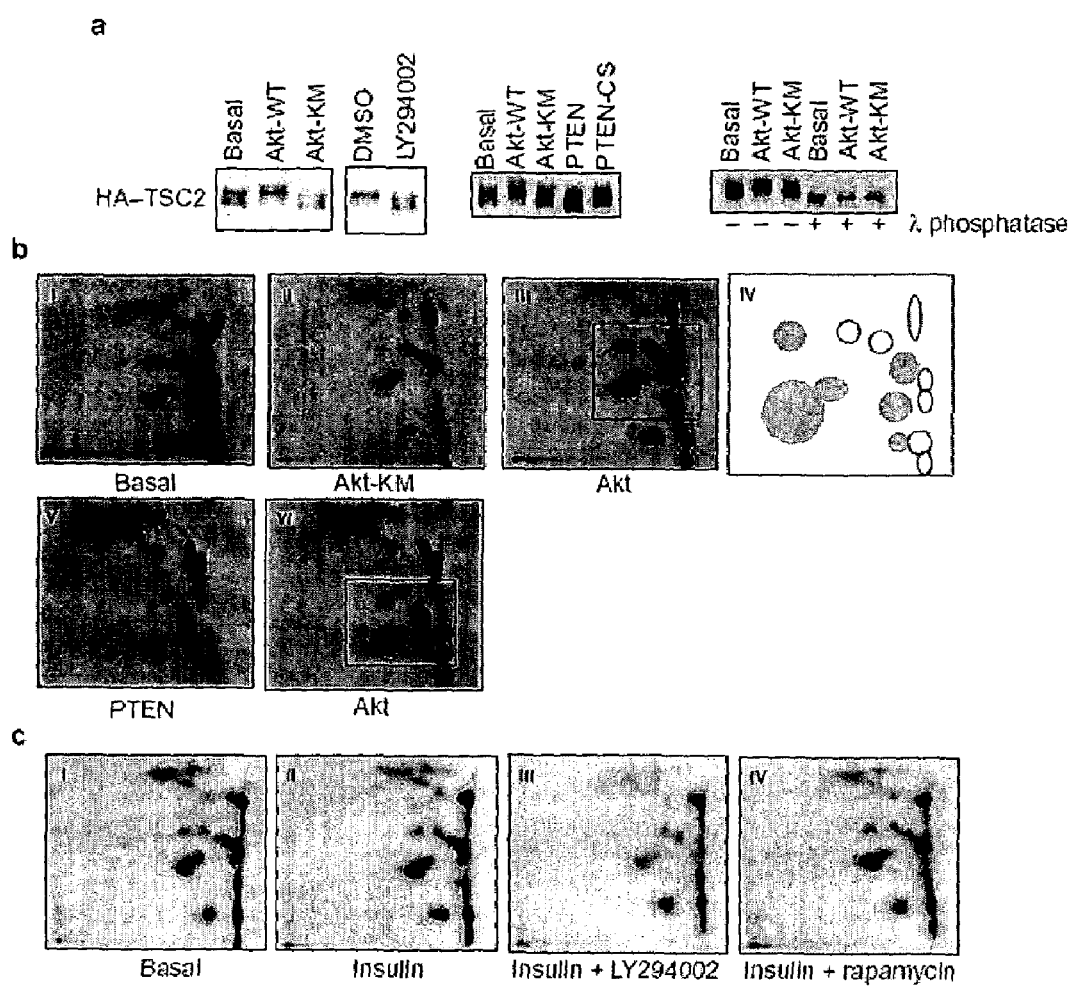
FIG. 3 shows phosphorylation of TSC2 by Akt.

Although genetic studies in Drosophila have established that dTsc1–dTsc2 antagonizes the function of the IR in the control of cell growth, the precise functions of dTsc1–dTsc2 in this pathway are unclear. Genetic evidence also indicates that dTsc1–dTsc2 may function downstream of, or parallel to, Akt (Gao and Pan, *Genes Dev.* 15, 1383–1392 (2001); Potter et al., *Cell* 105, 357–368 (2001)). To distinguish between these two possibilities, the effect of Akt on TSC1 and TSC2 was examined. Co-expression of Akt, but not the kinase-inactive mutant, Akt-KM, resulted in an accumulation of slow-migrating forms of TSC2, showing that Akt enhances phosphorylation of TSC2 (FIG. 3a). By contrast, Akt had no effect on TSC1. In addition, treatment with the PI(3)K inhibitor, LY294002, which blocks endogenous activation of Akt, also increased the mobility of TSC2. Furthermore, experiments with PTEN, or a catalytically inactive mutant, PTEN-CS, also supported the idea that Akt is responsible for phosphorylation of TSC2. Expression of PTEN, but not PTEN-CS, increased the mobility of TSC2 (FIG. 3a). Treatment with phosphatase confirmed that the mobility shift was a result of phosphorylation (FIG. 3a).

To characterize the phosphorylation of TSC2 by Akt, in vivo 32P-labelling and two-dimensional phosphopeptide mapping were performed. The results showed that TSC2 is phosphorylated at multiple sites in vivo (FIG. 3b). Co-expression with Akt or PTEN affected a subset of phosphopeptides (FIG. 3b, panels V and VI). Akt increased the intensity of these phosphopeptides, whereas PTEN decreased the intensity. These results are also presented schematically (FIG. 3b, panel IV). The shaded spots denote phosphopeptides whose intensity is altered by co-expression of Akt or PTEN. Insulin stimulation slightly increased phosphorylation of the same phosphopeptides that are enhanced by Akt (FIG. 3c, panel II). Treatment with LY294002, which indirectly inhibits Akt, also decreased phosphorylation of the same subset of phosphopeptides (FIG. 3c, panel III). In contrast, inhibition of mTOR by rapamycin had no effect on the phosphorylation of TSC2 (FIG. 3c, panel IV). These results show that the insulin-Akt pathway is responsible for the phosphorylation of TSC2, whereas mTOR or S6K are not involved.

Mutation Analysis of TSC2

Figure 4:
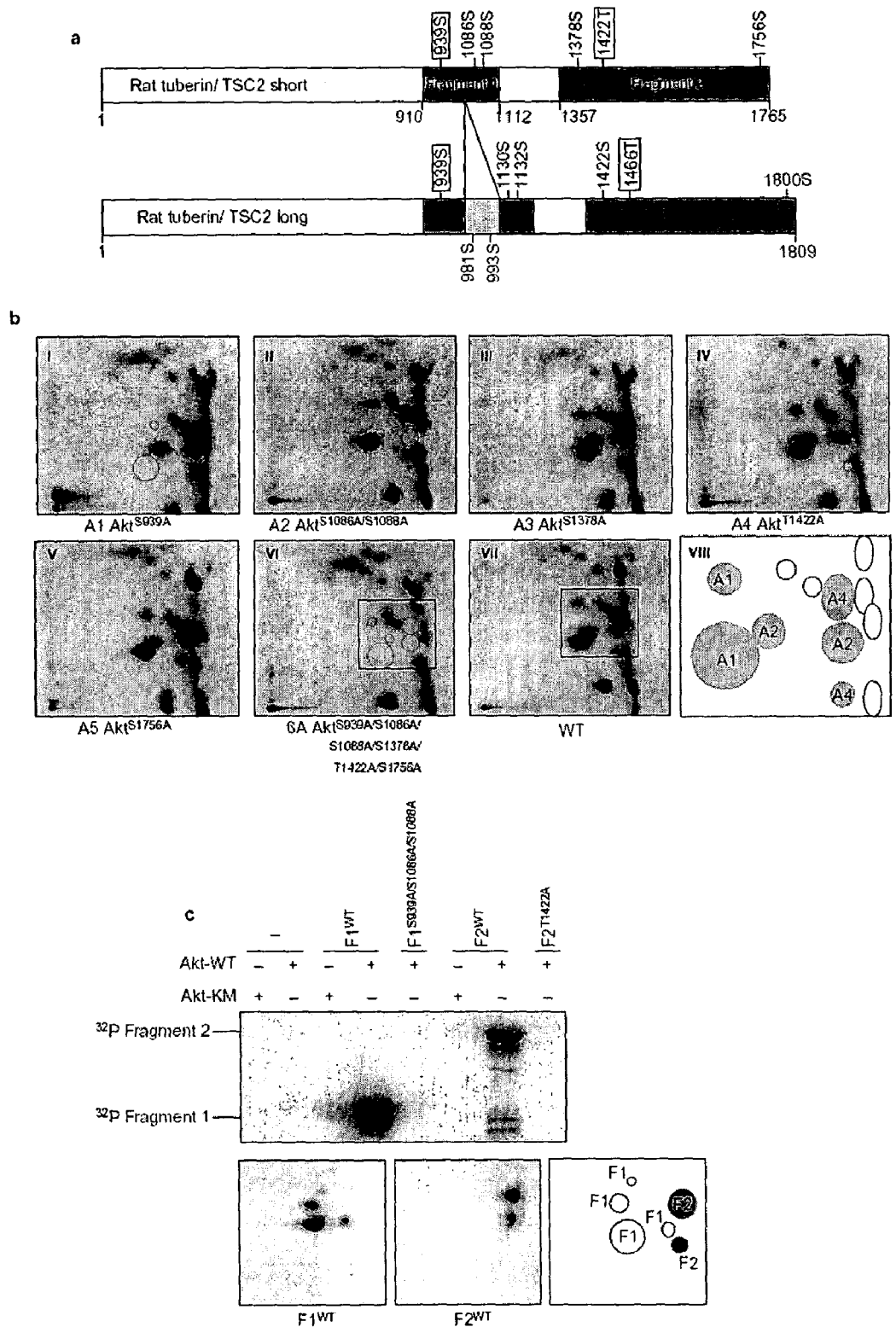
FIG. 4 shows the determination of Akt-dependent phosphorylation sites in TSC2.

Sequence analysis of TSC2 demonstrated that it contains eight putative Akt consensus phosphorylation sites (Datta et al., *Genes Dev.* 13, 2905–2927 (1999)), of which two are conserved in dTsc2 (FIG. 4a). A rat TSC2 cDNA that has an internal deletion of two putative Akt sites was obtained. This short form of TSC2, also identified in several clones in the expression sequence tag (EST) database, was used in this study. To further examine the phosphorylation of TSC2, the six putative Akt phosphorylation sites (FIG. 4a) were mutated individually (A1–A5) or in combination (6A), (FIG. 4b). Mutation of Ser 939 (A1; panel I), Ser 1086/Ser 1088 (A2; panel II), Thr 1422 (A4; panel IV), but not Ser 1378 (A3; panel III) nor Ser 1756 (A5; panel V), affected the phosphopeptide pattern of TSC2 (FIG. 4b). The phosphopeptides that disappeared in the 6A mutant (panel VI) are represented as shaded spots in panel VIII. The pattern of these phosphopeptides matched precisely with those altered by co-expression of Akt or PTEN (compare FIG. 3b, panel IV with FIG. 4b, panel VIII) or treatment with LY294002 (FIG. 3c, panel III). These data demonstrate that Ser 939, Ser 1086/Ser 1088 and Thr 1422 are required for proper in vivo phosphorylation of TSC2. The present invention is not limited to a particular mechanism. Indeed, an understanding of the mechanism is not necessary to practice the present invention. Nonetheless, it is contemplated that these sites are the Akt-dependent phosphorylation sites.

To show that Akt phosphorylates TSC2 on the residues identified above, it was examined whether Akt phosphorylated TSC2 in vitro using purified recombinant proteins. Glutathione S-transferase (GST)-Akt was purified from transfected HEK293 cells, whereas TSC2 fragments 1 and 2 were expressed in *Escherichia coli* and purified. Wild-type Akt, but not the kinase-inactive Akt-KM mutant, efficiently phosphorylated both fragment 1 and fragment 2 of TSC2 in vitro (FIG. 4a,c). Furthermore, mutation of Ser 939, Ser 1086 and Ser 1088 in fragment 1, and mutation of Thr 1422 in fragment 2, eliminated Akt-dependent phosphorylation in vitro (FIG. 4c). The data show that Akt directly phosphorylates TSC2 on multiple sites, both in vitro and in vivo.

Figure 5:
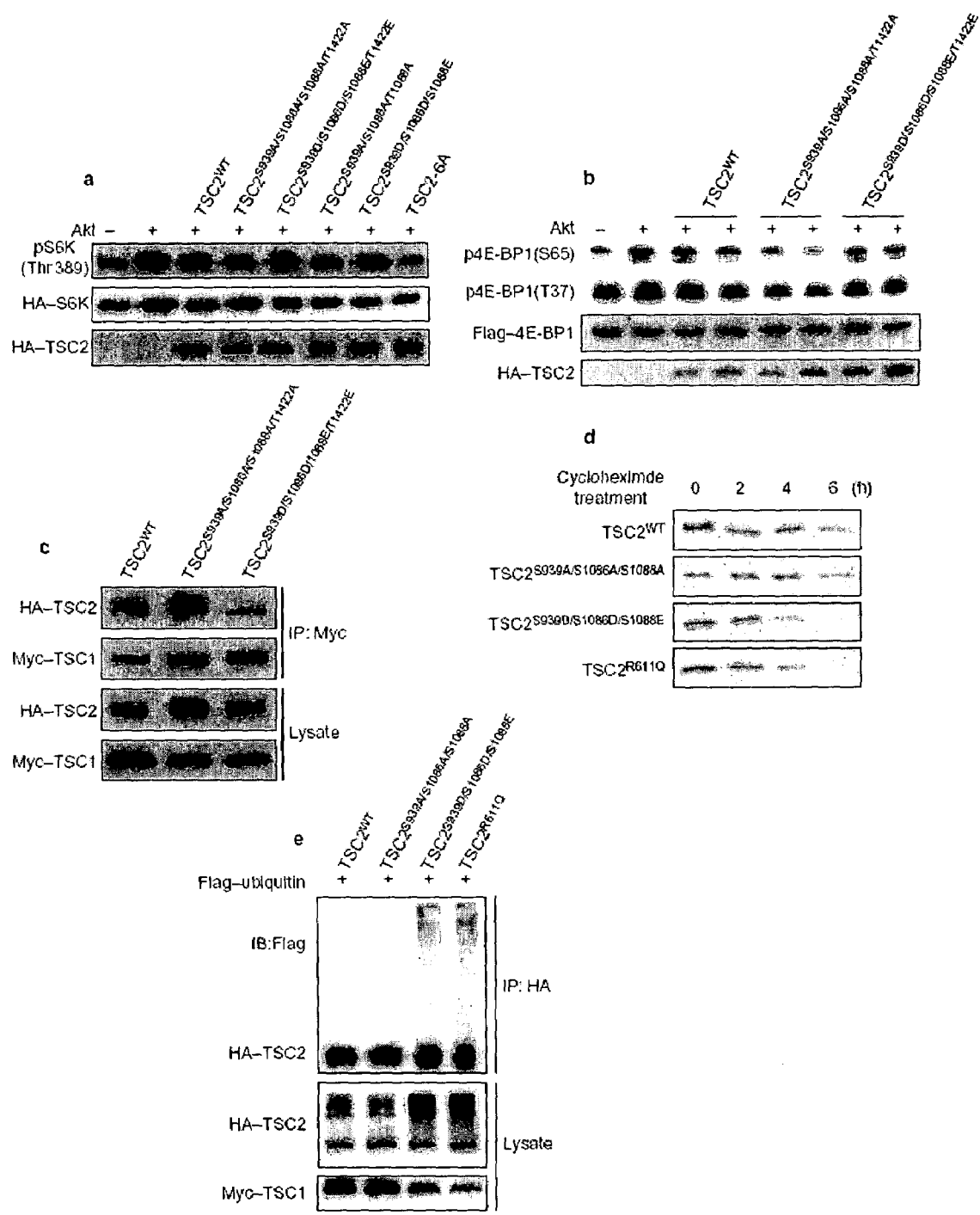
FIG. 5 shows that mutation of Akt phosphorylation sites alters TSC2 activity.

On the basis of the opposing functions of Akt and TSC2 in cell growth control in Drosophila, it is plausible that phosphorylation by Akt inhibits TSC2 function. Mutation of the Akt phosphorylation sites to alanine enhanced the ability of TSC2 to inhibit S6K, whereas mutation to phosphomimetic acidic residues decreased the inhibitory activity of TSC2 (FIG. 5a). Another downstream target of the Akt signaling pathway is 4E-BP1, which is involved in PI(3)K/Akt-induced regulation of cell growth (Miron et al. *Nature Cell Biol.* 3, 596–601 (2001)). Consistently, the phosphomimetic TSC2 mutant was less effective than the alanine mutant in inhibiting phosphorylation of 4E-BP1 (FIG. 5b). The present invention is not limited to a particular mechanism. Indeed, an understanding of the mechanism is not necessary to practice the present invention. Nonetheless, it is contemplated that these data show that Akt dependent phosphorylation inhibits TSC2 function. The formation of a complex between TSC1 and TSC2 is important for their biological functions. Disease-associated mutations in TSC2 weaken the interaction with TSC1 (FIG. 2c), which further supports the functional importance of TSC1–TSC2 complex formation. It was also found that the phosphorylation mimetic mutations of the Akt sites in TSC2 weakened its interaction with TSC1, as determined by coimmunoprecipitation experiments (FIG. 5c). Free TSC2 is unstable as a result of its susceptibility to ubiquitin-dependent degradation, whereas formation of the TSC1–TSC2 complex stabilizes TSC2 (Benvenuto et al., *Oncogene* 19, 6306–6316 (2000)). The phosphomimetic TSC2 mutant was consistently expressed at a lower level than the wild type or the TSC2 alanine mutant when same amount of DNA was used for transfection. The phosphorylation mimetic mutant of TSC2, similar to the disease-derived TSC2R611Q mutant, was less stable than wild-type TSC2 or the alanine mutant (FIG. 5d). Ubiquitination of TSC2 mutants was examined in the presence of 10 M MG132, an inhibitor of proteosome-dependent protein degradation. As expected, the phosphomimetic mutant was ubiquitinated, whereas wild type TSC2 and the alanine substitution mutant were ubiquitinated to a lesser degree (FIG. 5e). Similarly, the disease-derived TSC2R611Q mutant was also highly ubiquitinated. Therefore, Akt-dependent phosphorylation inhibits the function of TSC2 by destabilizing its association with TSC1, thus promoting ubiquitin-mediated degradation.

Nutrient Stimulation

Figure 6:
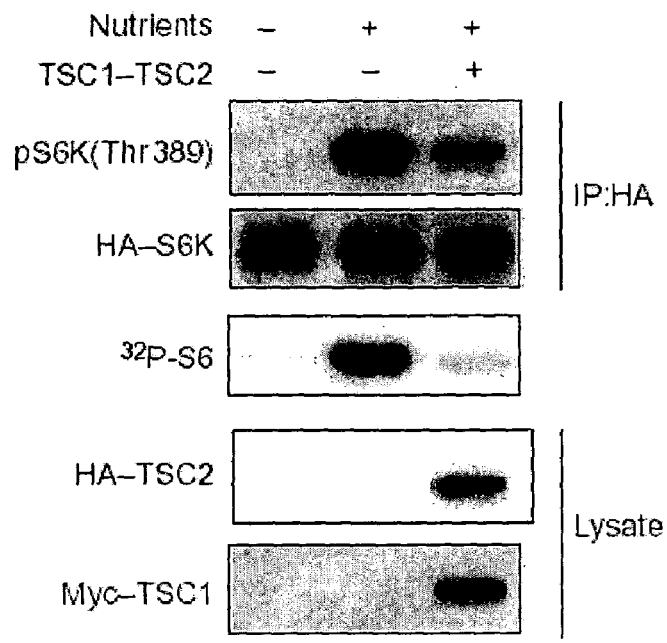
FIG. 6 shows inhibition of nutrient-stimulated phosphorylation and kinase activity of S6K by TSC1–TSC2.
Figure 6:
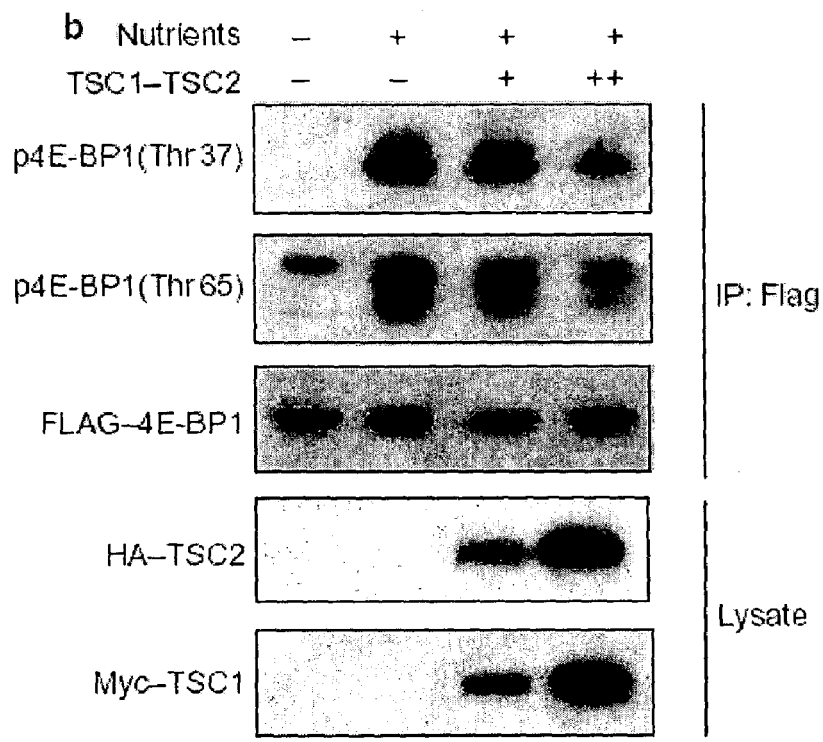

Nutrient stimulation activates S6K and inactivates 4E-BP1 (Shah et al., *Am. J. Physiol. Endocrinol. Metab.*279, E715–E729 (2000)). Nutrient-induced phosphorylation of S6K and 4E-BP1 is blocked by rapamycin, indicating a major role for mTOR in nutrient signaling. In contrast, nutrient stimulation has no effect on activation of Akt35. The nutrient-stimulated phosphorylation and kinase activity of S6K was inhibited by TSC1–TSC2 (FIG. 6a), showing that TSC1–TSC2 is also involved in the nutrient response. Inhibition of S6K activity was observed under conditions where much less TSC1–TSC2 protein was expressed, compared with S6K. A direct interaction between S6K and TSC1–TSC2 was not detected and TSC1–TSC2 selectively inhibited phosphorylation of Thr 389, the rapamycin-sensitive site in S6K (FIG. 1b). Phosphorylation of 4E-BP1 is sensitive to inhibition with rapamycin, and mTOR has been shown to directly phosphorylate 4E-BP1 (Gingras et al., *Genes Dev.* 13, 1422–1437 (1999)). Co-expression of TSC1–TSC2 also inhibited the phosphorylation of 4E-BP1 in response to stimulation with nutrients (FIG. 5b). The present invention is not limited to a particular mechanism. Indeed, an understanding of the mechanism is not necessary to practice the present invention. Nonetheless, it is contemplated that, together, these observations show that TSC1–TSC2 may function through mTOR to regulate the phosphorylation of S6K and 4E-BP1.

To examine a role for mTOR in the function of TSC1–TSC2, the rapamycin-resistant mutants, S6K-dC104 and S6KdNC were analyzed (Dennis et al. *Science* 294, 1102–1105 (2001); Weng et al., *Mol. Cell. Biol.* 15, 2333–2340 (1995); each of which is herein incorporated by reference). S6K-dC104 contains a C-terminal deletion and phosphorylation of Thr 389 in S6K-dC104 is inhibited by LY249002, but not by rapamycin (Dennis et al. supra). In contrast, the kinase activity of S6K-dC104 is inhibited by rapamycin (Weng et al., supra; Schalm et al., *Curr. Biol.* 12, 632–639 (2002)). Consistent with the reported observations, phosphorylation of Thr 389 in S6K-dC104 was inhibited by wortmannin or LY294002, but not by rapamycin (FIG. 7a). TSC1–TSC2 inhibited neither the basal nor the insulin-stimulated phosphorylation of Thr 389 in S6K-dC104 (FIG.7b). The kinase activity of S6K-dC104 was inhibited by TSC1–TSC2 (FIG. 7c). These results indicate that the effects of TSC1–TSC2 mimic the effects of rapamycin. The N-terminal region of S6K contains the TOR signaling (TOS) motif (Schalm et al., supra). Deletion of the TOS motif severely decreases kinase activity and eliminates stimulation by mTOR. However, further deletion of the C terminus partially rescues the kinase activity of the N-terminal deletion and renders S6K-dNC completely resistant to rapamycin (Schlam et al., supra). The kinase activity of S6K-dNC was also resistant to inhibition by TSC1–TSC2 (FIG. 7c). The effects of TSC1–TSC2 on S6K mutants strictly correlate with the effects of rapamycin, and therefore support a model in which TSC1–TSC2 and mTOR function in the same pathway.

To determine the effect of TSC1–TSC2 on mTOR, an in vitro kinase assay of immunoprecipitated mTOR was determined. Cotransfection of TSC1–TSC2 inhibited the ability of mTOR kinase to phosphorylate Thr 389 of S6K (FIG. 7d), showing that mTOR activity is inhibited by TSC1–TSC2. To further test the effect of TSC1–TSC2 on mTOR activity, phosphorylation of mTOR at Ser 2448, which has been implicated in mTOR activation (Nave et al., *Biochem J.* 344, 427–431 (1999)), was examined. The results demonstrated that overexpression of TSC1–TSC2 inhibited phosphorylation of Ser 2448 in mTOR in a dose-dependent manner (FIG. 7e). Furthermore, a decrease of endogenous TSC2 by RNAi caused an increase in Ser 2448 phosphorylation in mTOR (FIG. 7e), supporting a negative role for endogenous TSC1–TSC2 in the regulation of mTOR. Akt has been suggested to phosphorylate Ser 2448 in mTOR (Nave et al., supra; Scott et al., *Proc. Natl Acad. Sci. USA* 95, 7772–7777 (1998); Sekulic et al., *Cancer Res.*60, 3504–3513 (2000)). The present invention is not limited to a particular mechanism. Indeed, an understanding of the mechanism is not necessary to practice the present invention. Nonetheless, it is contemplate that, because activation of Akt is not inhibited by TSC1–TSC2, the TSC1–TSC2-mediated inhibition of mTOR phosphorylation at Ser 2448 is a result of competition for the common kinase, Akt. It is also possible that TSC1–TSC2 blocks the accessibility of mTOR to Akt and/or enhance the dephosphorylation of mTOR.

ATP Depletion Induces TSC2 Phosphorylation

Figure 8:
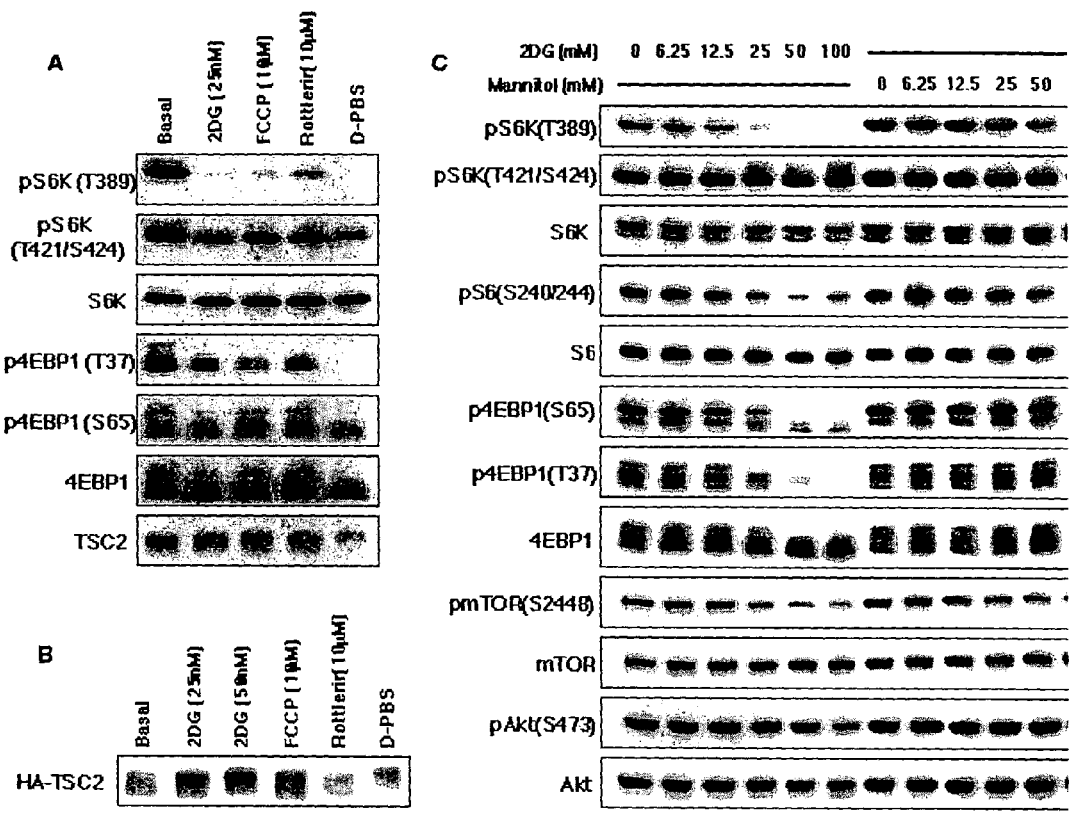
FIG. 8 shows the effects of energy depletion on phosphorylation of S6K, S6, 4EBP1, mTOR, Akt, AMPK, and TSC2 by 2-DG.
Figure 8:
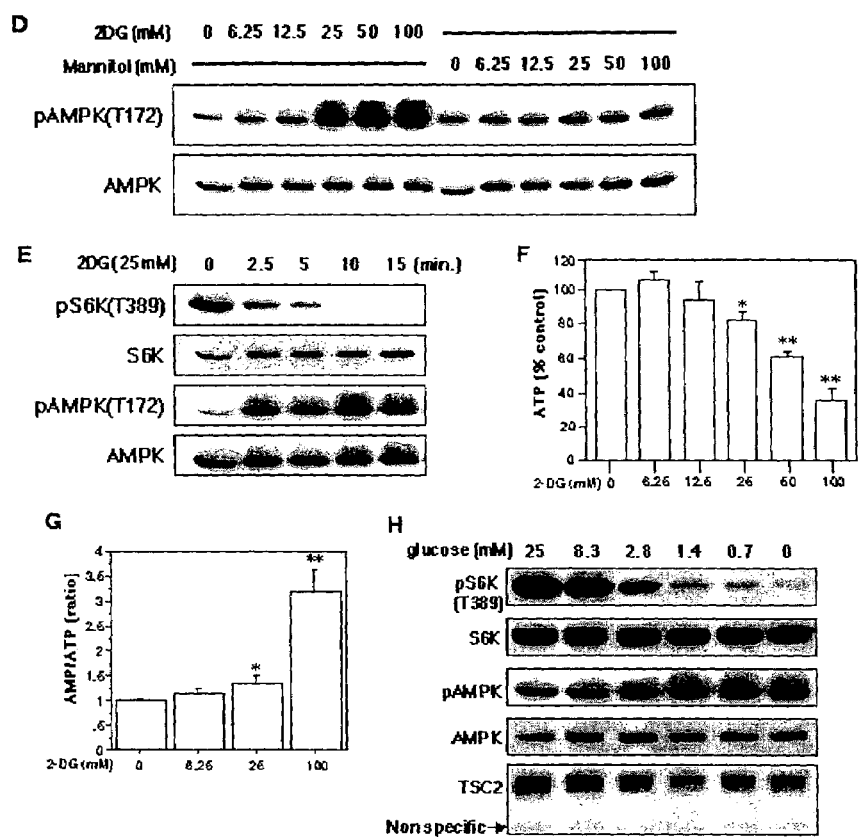

Protein synthesis is regulated by multiple cellular conditions including cellular energy level. It was observed that depletion of cellular ATP by the glucose analog 2-deoxyglucose (2-DG, which blocks cellular glucose utilization by indirectly inhibiting hexokinase), mitochondrial uncoupler FCCP, and the PKC inhibitor Rottlerin (Soltoff, *J. Biol. Chem.* 276:37986–37992 (2001) caused a dephosphorylation of S6K and 4EBP1 (FIG. 8A). In addition, depletion of nutrients by culturing cells in D-PBS inhibited the phosphorylation of S6K and 4EBP1 (Hara et al., 1998). ATP depletion and nutrients deprivation also resulted in a significant mobility upshift of TSC2 when resolved on a 5% SDS-PAGE gel (FIG. 8B), indicating that TSC2 phosphorylation was possibly enhanced by these cellular conditions.

It has previously been reported that 2-DG treatment using concentrations between 20 and 100 mM achieved 20 to 50% reduction of intracellular ATP levels and resulted in inhibition of S6K and 4EBP1 phosphorylation (Dennis et al., 2001). It was concluded that the inhibition of S6K and 4EBP1 phosphorylation by 2-DG is directly due to the sensing of lowered ATP levels by MTOR, which has a $K_m$ for ATP of around 1 mM (Dennis et al., 2001). Experiments conducted during the course of development of the present invention observed that mannitol, an osmolite, at 100 mM also significantly inhibited the phosphorylation of S6K (FIG. 8C), showing that the effect of high concentration of 2-DG is due to a mixed response of depletion of cellular ATP level and its acting as an osmolite. It was further observed that at low concentrations of 2-DG, such as 25 mM, phosphorylation of S6K on T389 was effectively inhibited while a similar concentration of mannitol had little effect (FIG. 8C). Similar observations were observed with the phosphorylation of S6 and 4EBP1 (FIG. 8C). Phosphorylation of mTOR S2448, which correlates with mTOR activity (Nave et al., 1999; Scott et al., *Proc. Natl. Acad. Sci.* 95:7772–7777 (1998); Sekulic et al., 2000), was also inhibited by 25 mM 2-DG (FIG. 8C). In contrast, 25 mM 2-DG had little effect on Akt phosphorylation (FIG. 8C). The present invention is not limited to a particular mechanism. Indeed, an understanding of the mechanism is not necessary to practice the present invention. Nonetheless, it is contemplated that these results demonstrate that 2-DG specifically inhibits the phosphorylation of S6K, 4EBP1 and mTOR but does not signal through Akt.

AMPK is more sensitive to changes in cellular energy status than mTOR because it is activated by the ratio of AMP/ATP. 25 mM 2-DG activated AMPK as indicated by the dramatic increase of T172 phosphorylation in AMPK (FIG. 8D). 2-DG at 25 mM induced rapid AMPK activation and concomitant dephosphorylation of S6K as a function of treatment time (FIG. 8E). These data are consistent with recent reports that AMPK activation closely correlates with the inhibition on S6K and 4EBP1 (Horman et al., 2002; Kimura et al., 2003; Krause et al., 2002). The present invention is not limited to a particular mechanism. Indeed, an understanding of the mechanism is not necessary to practice the present invention. Nonetheless, it is contemplated that these data show that activation of AMPK may be responsible for the ATP-depletion induced dephosphorylation of S6K and 4EBP1. A statistically significant reduction of ATP levels and an increase of AMP/ATP ratio in cells treated with 25 mM 2-DG was observed (FIG.8F, G). However, based on previously published data, a decrease in ATP concentration does not significantly affect mTOR kinase activity (Dennis et al., 2001). The present invention is not limited to a particular mechanism. Indeed, an understanding of the mechanism is not necessary to practice the present invention. Nonetheless, it is contemplated that AMPK is the prime energy sensor in response to mild energy depletion. Glucose limitation also decreased S6K phosphorylation, increased AMPK phosphorylation, and caused a mobility shift of TSC2 (FIG. 8H).

2-DG Stimulates The Interaction Between Endogenous AMPK And TSC2

Figure 9:
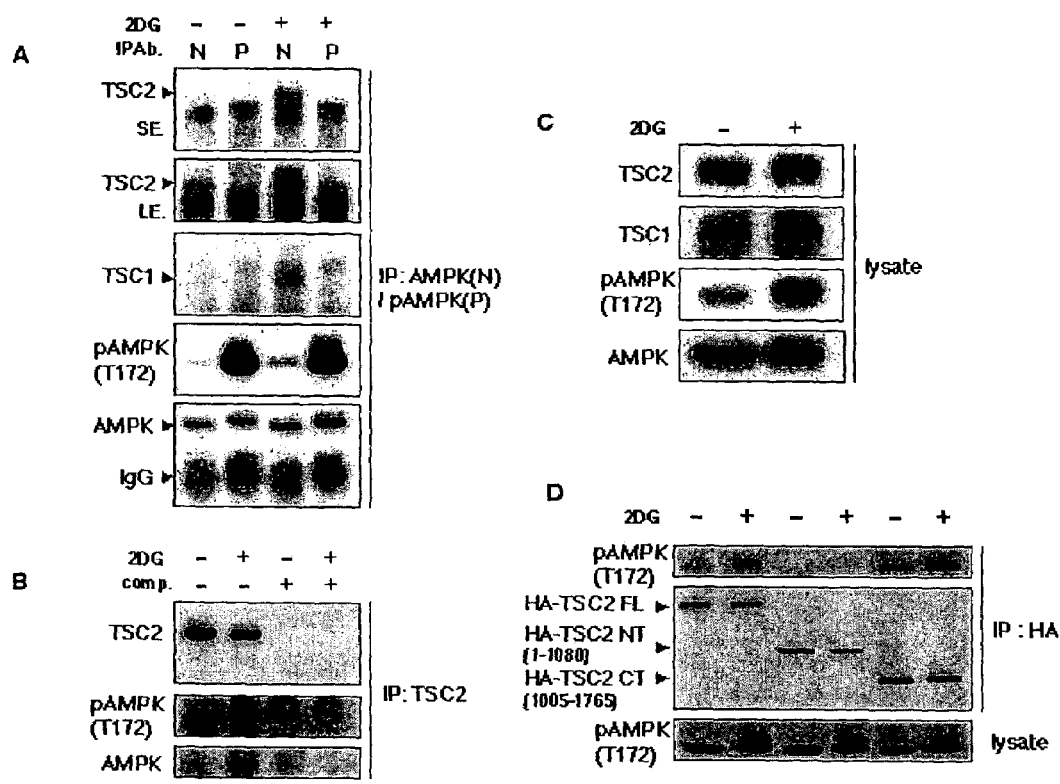
FIG. 9 shows 2-DG stimulates the interaction of endogenous AMPK and TSC2.

To determine if AMPK is responsible for TSC2 phosphorylation, the presence of AMPK and TSC2 interaction was examined. Immunoprecipitation of AMPK indicated that both TSC1 and TSC2 are weakly co-immunoprecipitated by AMPK (FIG. 9A). TSC2 and TSC1 were found to interact preferentially with AMPK following 2-DG stimulation. Co-immunoprecipitations with the anti-phospho AMPK antibody (PAMPK) which recognizes the active form of AMPK was also performed. This antibody specifically precipitated the active form of AMPK from both control and 2-DG treated cell lysates (FIG. 9A). However, no TSC2 or TSC1 was recovered in the anti-pAMPK immunoprecipitates. This observation is not surprising because T172 in AMPK is localized in the activation loop (Scott et al., *J. Mol. Bio.* 317:309–323 (2002); Stein et al., *Biochem. J.* 345(part3): 437–443 (2000). The present invention is not limited to a particular mechanism. Indeed, an understanding of the mechanism is not necessary to practice the present invention. Nonetheless, it is contemplated that these results demonstrate that binding of AMPK to the activation loop may block substrate binding based on known kinase structures.

To determine whether active AMPK is associated with TSC2, reciprocal co-immunoprecipitation with anti-TSC2 antibody followed by Western blotting with anti-AMPK and anti-pAMPK antibody was performed. It was observed that the interaction between endogenous AMPK and TSC2 was enhanced by 2-DG (FIG. 9B). The interaction was effectively competed by prior-incubation of TSC2 antibody with competing peptide, demonstrating the specificity of the co-immunoprecipitation (FIG. 9B). FIG. 9C shows that the levels of proteins in the lysates are similar. The above observations demonstrate that 2-DG treatment stimulates the interaction between endogenous TSC2 and AMPK.

Co-immunoprecipitation studies between endogenous AMPK and overexpressed TSC2 and confirmed that 2-DG enhances the interaction between TSC2 and AMPK was also performed (FIG. 9D). Deletion analysis showed that the C-terminal domain of TSC2 is responsible for the interaction with AMPK while the N-terminal domain is not required.

TSC2 is Required to Mediate the Cellular Energy Response

To determine the role of TSC2 in S6K inactivation by 2-DG, HEK293 cells were treated with TSC2 RNAi oligos. TSC2 RNAi significantly decreased endogenous TSC2 protein levels, but had no effect on the unrelated protein MEK2 (FIG. 10A). 2-DG induced S6K dephosphorylation was blocked in TSC2 knockdown cells, but not in the control cells. In contrast, knockdown of TSC2 had no significant effect on AMPK phosphorylation in response to 2-DG. Inhibition of mTOR by rapamycin blocked S6K phosphorylation even when TSC2 expression was knocked down showing that mTOR is downstream of TSC2 (FIG. 10B).

The function of AMPK in S6K regulation was further examined. Co-expression of the active AMPK αI or αII catalytic subunit resulted in a decrease of S6K phosphorylation (FIG. 10C). The present invention is not limited to a particular mechanism. Indeed, an understanding of the mechanism is not necessary to practice the present invention. Nonetheless, it is contemplated that AMPK negatively controls S6K phosphorylation. Knockdown of TSC2 by RNAi blocked the inhibitory effect of AMPK expression showing that TSC2 acts downstream of AMPK. Neither TSC2 RNAi nor rapamycin affected the phosphorylation of acetyl CoA carboxylase (ACC) and eukaryote elongation factor 2 (eEF2), two AMPK substrates (FIG. 10D, E), supporting the specific role of TSC2 in mediating AMPK on S6K regulation.

It was hypothesized that if TSC2 plays a role in mediating S6K inhibition by ATP depletion, than EEF8 (TSC2−/−) and the EEF4 (TSC2+/+) fibroblasts should respond differently to various ATP depletion reagents. As expected, EEF8 cells show a much higher level of S6K phosphorylation (FIG. 10F). In order to compare the results of EEF4 and EEF8 cells, both long and short exposures of the S6K phosphorylation immunoblot are presented in FIG. 10F. It was observed that Rottlerin, FCCP, and to a lesser extent, azide, oligomycin and rotenone caused a decrease in S6K phosphorylation in EEF4 cells. The effects of these reagents on S6K phosphorylation are much weaker in EEF8 cells (FIG. 10F). Similar results were observed with the phosphorylation of 4EBP1. However, the activation of AMPK was not different between the EEF4 and the EEF8 cells (FIG. 10F). The present invention is not limited to a particular mechanism. Indeed, an understanding of the mechanism is not necessary to practice the present invention. Nonetheless, it is contemplated that TSC2 plays an important role in mediating the effect of ATP depletion on the phosphorylation of S6K and 4EBP1. Similar experiments with 2-DG and D-PBS treatment was performed. In EEF8 (TSC2−/−) cells, 2-DG and D-PBS had little effect on 4EBP1 phosphorylation. This is in contrast to the inhibition of phosphorylation of 4EBP1 in the EEF4 (TSC2+/+) cells (FIG. 10G). The present invention is not limited to a particular mechanism. Indeed, an understanding of the mechanism is not necessary to practice the present invention. Nonetheless, it is contemplated that these data are consistent with previously published observations that nutrient depletion-induced S6K dephosphorylation is compromised in TSC2−/−cells (Gao et al., *Nat. Cell Biol.* 4:699–704 (2002).

TSC2 Is Phosphorylated By AMPK

Figure 11:
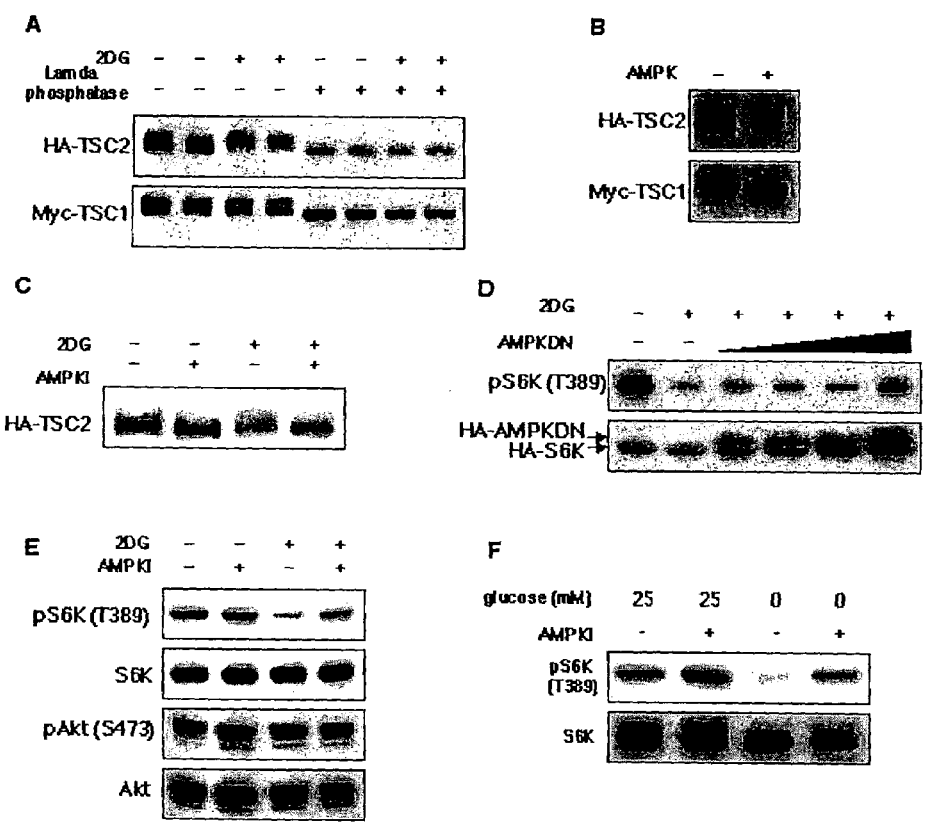
FIG. 11 shows ATP depletion and AMPK induce TSC2 phosphorylation.

Treatment with lambda phosphatase converted TSC2 to a faster migrating band (FIG. 11A), showing that the 2-DG-induced mobility shift is due to phosphorylation. TSC1 is also a phosphoprotein which is downshifted by lambda phosphatase treatment (FIG. 11A). However, 2-DG treatment did not alter the mobility of TSC1. Co-transfection of active AMPK αI also induced a mobility upshift of TSC2, but not of TSC1 showing that AMPK regulates TSC2 phosphorylation (FIG. 11B). The AMPK inhibitor (compound C) was used to determine whether endogenous AMPK is involved in TSC2 phosphorylation (Zhou et al., *J. Clin. Invest.* 108:1167–1174 (2001). Incubation of HEK293 cells with 10 μM AMPK inhibitor increased the mobility of TSC2, supporting a role for endogenous AMPK in TSC2 phosphorylation (FIG. 11C).

The functional relationship between AMPK and 2-DG-induced S6K dephosphorylation was examined by expressing dominant negative AMPK. Dose-dependent expression of the kinase inactive catalytic subunit αII of AMPK (AMPK-DN) partially blocked S6K inhibition by 2-DG treatment (FIG. 11D). Furthermore, incubation of HEK 293 cells with an AMPK inhibitor significantly reversed the inhibitory effect of 2-DG on S6K phosphorylation (FIG. 11E). In contrast, treatment with the AMPK inhibitor had no effect on Akt phosphorylation. AMPK inhibitor also significantly blocked S6K dephosphorylation induced by glucose deprivation (FIG. 11F). The present invention is not limited to a particular mechanism. Indeed, an understanding of the mechanism is not necessary to practice the present invention. Nonetheless, it is contemplated that these data show that AMPK activation plays an important role in TSC2 phosphorylation and S6K inhibition in response to energy starvation.

T1227 And S1345 In TSC2 Are Major AMPK Phosphorylation Sites

To elucidate the mechanism of TSC2 regulation by AMPK, in vivo labeling and two dimensional phosphopeptide mapping of TSC2 was performed. Stimulation with 2-DG (25 and 40 mM) enhanced phosphorylation of several peptides (compare panels a, b, and c in FIG. 12A). Interestingly, co-expression of the active AMPK αI subunit also increased phosphorylation of the same peptides stimulated by 2-DG (compare panels a and d, FIG. 12A). The shaded spots in panel e denote phosphopeptides induced by 2-DG or AMPK. The present invention is not limited to a particular mechanism. Indeed, an understanding of the mechanism is not necessary to practice the present invention. Nonetheless, it is contemplated that these results clearly demonstrate that 2-DG treatment stimulates TSC2 phosphorylation and AMPK plays a major role in TSC2 phosphorylation.

Previously, the TSC2 sequence for AMPK recognition consensus sites was searched (Hardie et al., 1998) and it was found that rat TSC2 contains 8 putative AMPK sites. All putative AMPK sites were individually mutated and two-dimensional phosphopeptide mapping with each individual mutant was performed. These data indicate that all the individual mutants, except for T1227A and S1345A, had phosphopeptide maps similar to the wild type TSC2. The S1345A mutant affected the majority of the 2-DG and AMPK inducible phosphopeptides (spots 1, 2, 3, 5, 6, 7, 8 in panel f, FIG. 12A). The present invention is not limited to a particular mechanism. Indeed, an understanding of the mechanism is not necessary to practice the present invention. Nonetheless, it is contemplated that these results show that S1345 is likely an AMPK phosphorylation site in vivo. Furthermore, phosphorylation of S1345 affects phosphorylation of other residues, such as S1337 and S1341 which are adjacent to the AMPK site S1345 (FIG. 12B).

To confirm whether S1345 can be phosphorylated by AMPK directly in vitro, a TSC2 fragment containing S1345 was expressed and purified from *E. coli* (FIG. 12C). The TSC2 fragment was phosphorylated by immunoprecipitated AMPK, but not the kinase inactive AMPK mutant (FIG. 12C, top panel). Mutation of S1345 to either alanine (S1345A) or aspartate (S1345D) completely eliminated the in vitro phosphorylation of TSC2 by AMPK, indicating that S1345 is a direct AMPK phosphorylation site. The present invention is not limited to a particular mechanism. Indeed, an understanding of the mechanism is not necessary to practice the present invention. Nonetheless, it is contemplated that these data show that S1337 and S1341 are not direct AMPK phosphorylation sites (FIG. 12C) although phosphorylation of these residues is enhanced by 2-DG and AMPK (FIG. 12A, B). In order to confirm that the in vitro AMPK phosphorylation sites are also phosphorylated in TSC2 in vivo, the 2-dimensional phosphopeptide map of in vitro AMPK phosphorylated TSC2 was compared with that of the in vivo labeled TSC2 (FIG. 12D). Mixing of in vitro phosphorylated TSC2 fragment with the in vivo phosphorylated TSC2-S1345A mutant demonstrate that spots 3 and 6 are due to direct AMPK phosphorylation (FIG. 12D).

It was observed that spot 4 was eliminated and spot 9 was reduced in the TSC2-T1227A mutant (FIG. 12E, compare panels a and b). In vitro phosphorylation of the purified TSC2-F2 fragment by immunoprecipitated AMPK showed that AMPK specifically phosphorylates TSC2 on T1227 (FIG. 12F). Two dimensional phosphopeptide mapping confirmed that T1227 corresponds to spot 4 in the 2D map (FIG. 12E). The present invention is not limited to a particular mechanism. Indeed, an understanding of the mechanism is not necessary to practice the present invention. Nonetheless, it is contemplated that AMPK phosphorylates TSC2 on T1227.

Mutation of S1345 affected multiple phosphorylation sites including S1337 and 1341 even though these are not AMPK consensus (FIG. 12A, B). The TSC2-S1337/1341/1345A (TSC2–3A) triple mutant was created and the mobility shift induced by 2-DG was tested. The 2-DG dependent upshift was largely abolished in the triple mutant (FIG. 12G), indicating that these residues are major phosphorylation sites induced by energy depletion.

AMPK Phosphorylation Enhances TSC2 Function

The functional significance of AMPK phosphorylation was assessed by using TSC2 phosphorylation mutants. HEK 293 cells transfected with TSC2–3A mutant showed that this mutant was less able to inhibit S6K in response to 2DG treatment (FIG. 13A). This result is consistent with the notion that phosphorylation by AMPK promotes the ability of TSC2 to inhibit S6K. The ability of TSC2–3A to interact with TSC1 was also tested and the mutant TSC2 was found to be able to form a complex with TSC1 normally (FIG. 13B).

To examine whether phosphorylation of TSC2 by AMPK plays a role in the dephosphorylation of S6K and 4EBP1 in response to 2-DG treatment, EEF8 (TSC2−/−) fibroblast cells was transiently infected with a retrovirus expressing either the wild type or the T1227A/S1345A mutant. Expression of TSC2 reduced the basal phosphorylation of S6K and 4EBP1 (FIG. 13C). Treatment with 2-DG caused little decrease of S6K and 4EBP1 phosphorylation in the vector infected cells. In contrast, 2-DG significantly decreased S6K and 4EBP1 phosphorylation in wild type TSC2 expressing cells (FIG. 13C). Cells expressing the TSC2 T1227A/S1345A mutant were less responsive to 2-DG treatment than those expressing wild type TSC2 (FIG. 13C). The present invention is not limited to a particular mechanism. Indeed, an understanding of the mechanism is not necessary to practice the present invention. Nonetheless, it is contemplated that these data show that the AMPK-dependent phosphorylation of T1227 and S1345 in TSC2 plays an important role in the cellular response to 2-DG treatment.

To further establish the functional importance of TSC2 and AMPK phosphorylation in response to changes in the cellular energy, stable TSC2 expressing cell lines from the TSC2-/-LEF cells which are derived from an epithelial origin were established. Expression of TSC2 decreased S6K phosphorylation while expression of the TSC2-3A had a much weaker effect on S6K although both the wild type and the 3A mutant were expressed at a similar level (FIG. 13D). Glucose deprivation for 16 hours decreased S6K phosphorylation in the wild type TSC2 expressing cells, but had a much smaller effect in the vector or the TSC2-3A expressing cells even though AMPK activation is unaffected (FIG. 13E). The present invention is not limited to a particular mechanism. Indeed, an understanding of the mechanism is not necessary to practice the present invention. Nonetheless, it is contemplated that these results demonstrated that TSC2 is required for S6K inactivation by glucose deprivation. Furthermore, phosphorylation of TSC2 is required for the cellular response to energy limitation. Expression levels of TSC2 in retroviral infected LEF cells are slightly lower than the endogenous expression levels of TSC2 in HEK293 cells. Therefore, TSC2 are not over expressed in the stable cells used for the experiments.

TSC2 Protects Cells From Glucose Deprivation-Induced Apoptosis

Figure 14:
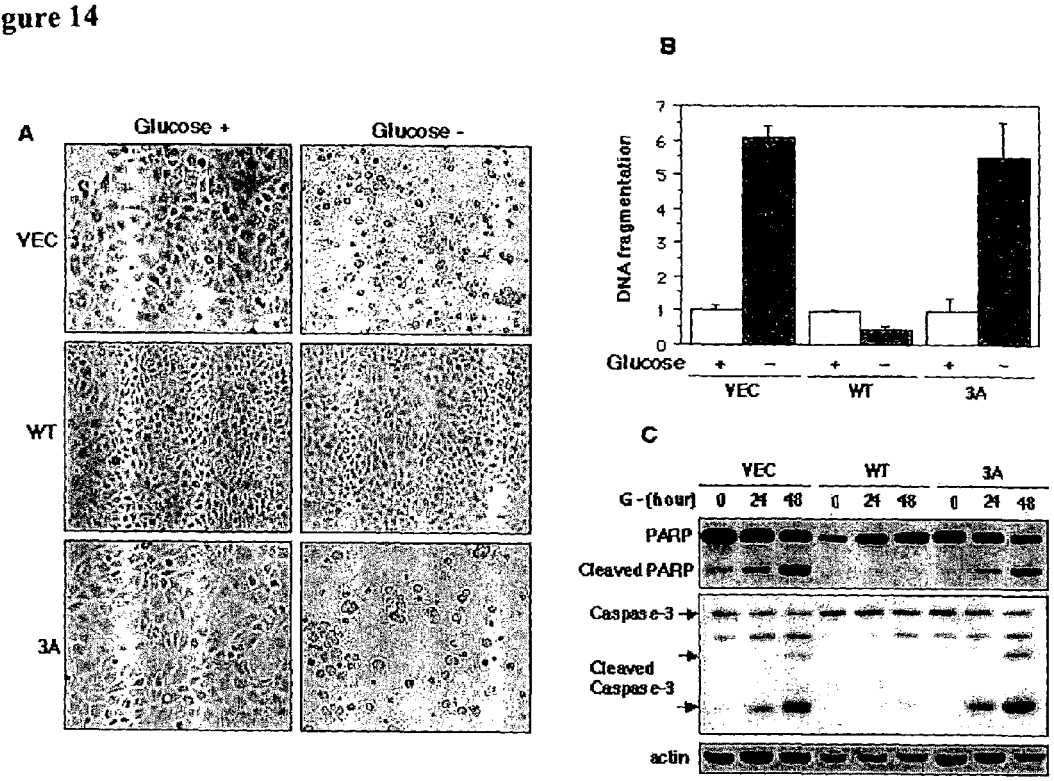
FIG. 14 shows TSC2 plays essential roles in protecting cells from glucose deprivation-induced apoptosis and cell size regulation.
Figure 14:
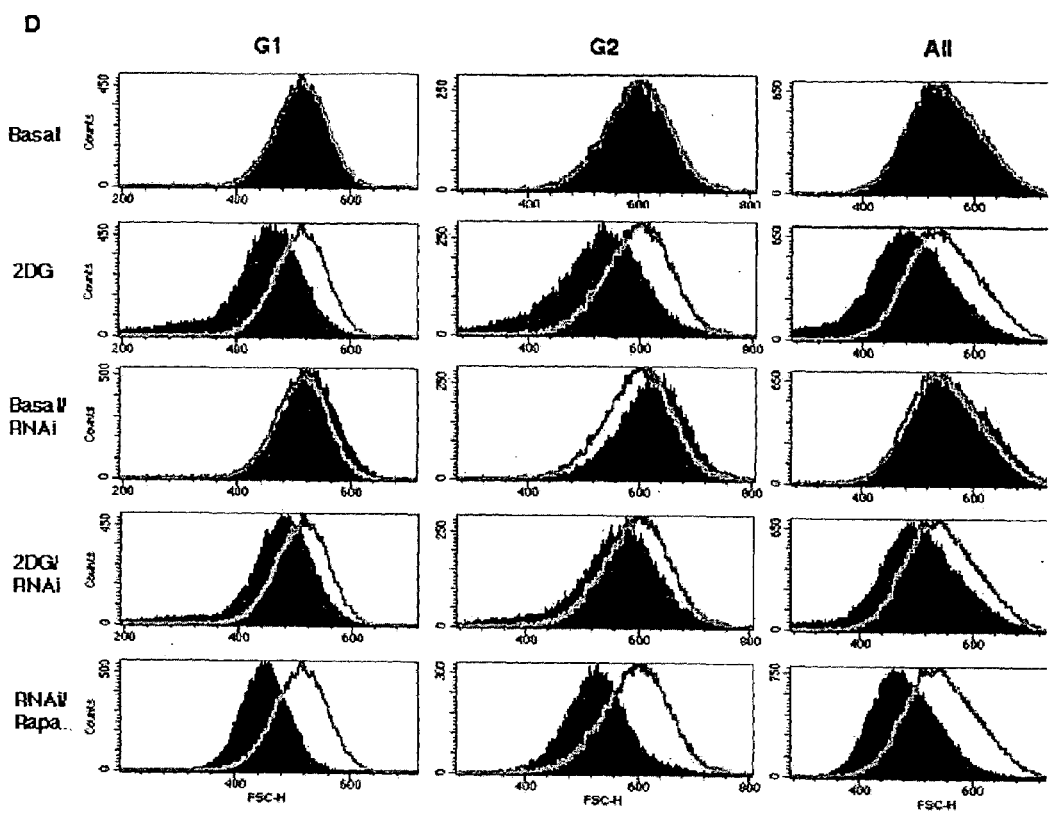
Figure 14:
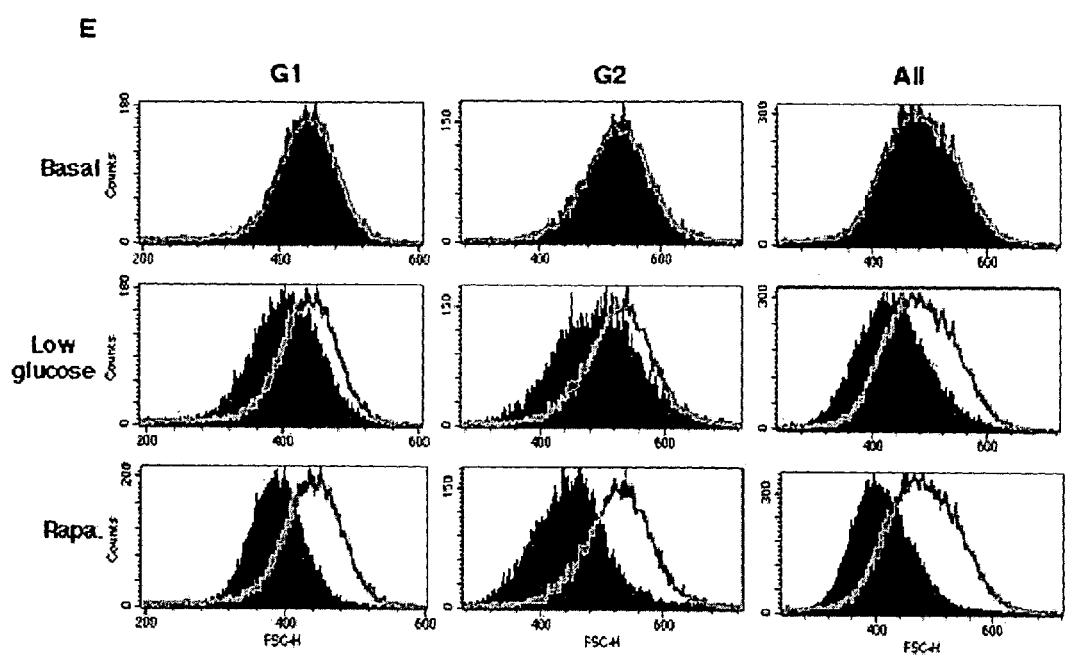
Figure 14:
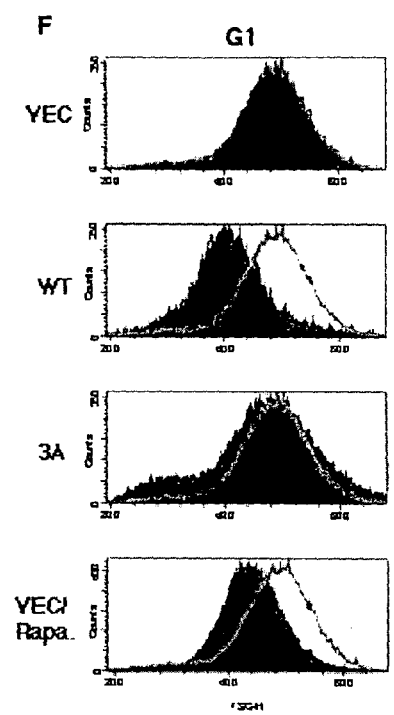
Figure 14:
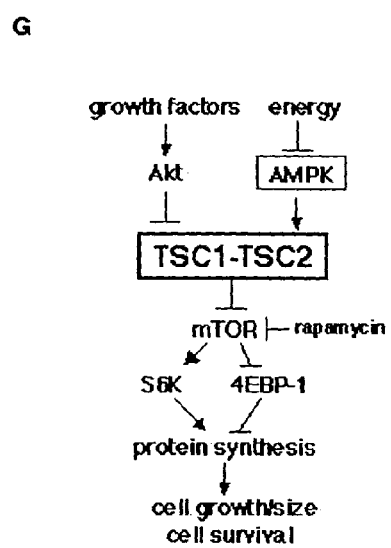

Vector infected LEF cells underwent massive cell death 72 hours after shifting to glucose free conditions (FIG. 14A). In contrast, the TSC2 expressing LEF cells showed little increase in cell death. Similarly, it was observed that the glucose deprivation induced cell death in EEF8 (TSC2-/-) but not in the control EEF4 (TSC2+/+) cells. The present invention is not limited to a particular mechanism. Indeed, an understanding of the mechanism is not necessary to practice the present invention. Nonetheless, it is contemplated that these results convincingly establish that TSC2 plays an essential to protect cells from energy starvation-induced cell death.

To determine the significance of AMPK phosphorylation in TSC2 function, the TSC2-3A expressing LEF cells was also examined. TSC2-3A failed to protect LEF cells from glucose deprivation-induced cell death (FIG. 14A). In contrast, etoposide, which induces apoptosis by DNA damage, caused cell death in both vector and wild type TSC2 expressing cells, indicating that TSC2 specifically participates in energy but not DNA damage responses. The present invention is not limited to a particular mechanism. Indeed, an understanding of the mechanism is not necessary to practice the present invention. Nonetheless, it is contemplated that these data demonstrate that phosphorylation of TSC2 by AMPK play a critical role to protect cells from glucose deprivation-induced cell death.

Experiments were also performed to further examine glucose deprivation induced apoptosis. A fluorescence based assay for DNA fragmentation showed that glucose deprivation induced apoptosis in vector and TSC2-3A, but not in TSC2 expressing LEF cells (FIG. 14B). Western blots for apoptosis markers revealed that both caspase 3 and PARP were cleaved during glucose deprivation-induced cell death, showing that cells are in fact undergoing apoptosis (FIG. 14C).

Cell Size Regulation By ATP Depletion And TSC2

TSC2 has been demonstrated to play a critical role in cell size control in Drosophila. It was observed that the knockdown of TSC2 by RNAi resulted in a reproducible increase in HEK293 cell size (FIG. 14D). The small effect of RNAi on cell size could be due to an incomplete elimination of TSC2 by RNAi. It was found that 2-DG treatment significantly decreased cell size (FIG. 14D). Knockdown of TSC2 by RNAi partially blocked the cell size effect induced by 2-DG. The cell size effects of TSC2 and 2-DG are cell cycle independent as these treatments similarly affect both G1 and G2 cells. The present invention is not limited to a particular mechanism. Indeed, an understanding of the mechanism is not necessary to practice the present invention. Nonetheless, it is contemplated that these results demonstrate that TSC2 plays an important role in 2-DG-induced cell size reduction.

The effect of glucose starvation on cell size was also investigated. HEK293 cells cultured in 2.8 mM glucose (normal medium has 25 mM glucose) for 72 hours showed a significant reduction of cell size (FIG. 14E). Treatment with rapamycin also decreased cell size as previously reported (Fingar et al., *Genes Dev.* 16:1472–1487 (2002). These data are consistent with that TSC2 mediates the energy limitation signal to regulate cell size.

It was also observed that TSC2 expressing LEF cells are significantly smaller than the vector or TSC2-3A expressing cells (FIG. 14A). FACS analysis studies confirmed that expression of TSC2 significantly decreased the size of LEF TSC2-/-cells (FIG. 14F). Interestingly, TSC2-3A showed a lessened ability to reduce cell size in the LEF TSC2-/-cells when compared to wild type TSC2. Rapamycin treatment was included as a control. The present invention is not limited to a particular mechanism. Indeed, an understanding of the mechanism is not necessary to practice the present invention. Nonetheless, it is contemplated that these observations are consistent with previous biological observations and provide the first convincing experimental evidence that TSC2 negatively regulates cell size in mammalian cells. Furthermore, these data demonstrate that the AMPK dependent phosphorylation plays an essential role for the physiological functions of TSC2.

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

I claim:

1. A method of treating a subject with tuberous sclerosis comprising administering to said subject an effective amount of an agent which targets defective cells having a defective TSC pathway, and reduces cellular ATP levels in said cells.

2. The method of claim 1, wherein said agent is mitochondrial uncoupler FCCP.

3. The method of claim 1, further comprising co-administration of rapamycin.

4. The method of claim 1, wherein said agent is rapamycin.

5. The method of claim 1, wherein said defective TSC pathway comprises a defective element of said TSC pathway selected from the group consisting of: TSC 1, TSC2, mTOR, S6K, and 4EBP-1.

6. The method of claim 1, wherein said agent is a hexokinase inhibitor.

7. The method of claim 1, wherein said agent is 2-deoxyglucose.

8. The method of claim 1, wherein said agent is a PKC inhibitor.

9. The method of claim 1, wherein said agent is Rottlerin.

10. The method of claim 1, wherein said agent is 5-aminoimidazole-4-carboxyamide ribonucleotide.

* * * * *